United States Patent
Miyama et al.

(10) Patent No.: US 11,197,788 B2
(45) Date of Patent: Dec. 14, 2021

(54) PACKAGING BODY FOR ABSORBENT ARTICLE

(71) Applicant: UNICHARM CORPORATION, Shikokuchuo (JP)

(72) Inventors: Takuya Miyama, Kanonji (JP); Satoru Sakaguchi, Kanonji (JP); Yasushi Kihara, Kanonji (JP); Takeshi Hanajiri, Kanonji (JP); Kayoko Kashiwagi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 128 days.

(21) Appl. No.: 16/343,405

(22) PCT Filed: Oct. 20, 2017

(86) PCT No.: PCT/JP2017/037934
§ 371 (c)(1),
(2) Date: Apr. 19, 2019

(87) PCT Pub. No.: WO2018/079425
PCT Pub. Date: May 3, 2018

(65) Prior Publication Data
US 2019/0336362 A1    Nov. 7, 2019

(30) Foreign Application Priority Data

Oct. 24, 2016 (JP) .............................. JP2016-208158
Oct. 24, 2016 (JP) .............................. JP2016-208161
Oct. 24, 2016 (JP) .............................. JP2016-208162

(51) Int. Cl.
*A61F 13/551*    (2006.01)
*B65D 85/07*     (2017.01)
*B65D 77/30*     (2006.01)

(52) U.S. Cl.
CPC .......... *A61F 13/5511* (2013.01); *B65D 85/07* (2018.01); *B65D 77/30* (2013.01); *B65D 2203/00* (2013.01)

(58) Field of Classification Search
CPC ..... A61F 13/5511; B65D 85/07; B65D 77/30; B65D 2203/00; B65D 75/5833; B65D 33/00; B65D 65/406
(Continued)

(56) References Cited

U.S. PATENT DOCUMENTS 7,220,053 B2 * 5/2007 Wu ..................... B65D 81/2038
                                                       383/100
7,270,861 B2 * 9/2007 Broering ............ A44B 18/0011
                                                       428/35.7
(Continued)

FOREIGN PATENT DOCUMENTS

AU    2015101209 A4    10/2015
JP    S48-36154 U      4/1973
(Continued)

OTHER PUBLICATIONS

Extended European Search Report in EP Application No. 17865545.2, dated Sep. 6, 2019, 8pp.
(Continued)

*Primary Examiner* — Ernesto A Grano
(74) *Attorney, Agent, or Firm* — Hauptman Ham, LLP

(57) ABSTRACT

A packaging body for absorbent articles which can further attract an attention of a user and can increase a desire of purchase of the user is provided. The packaging body for absorbent articles includes absorbent articles and a bag-shaped packaging sheet for packaging a plurality of absorbent articles. The packaging sheet includes a surface constituting an outer surface of the packaging body, and a back surface that constitutes an inner surface of the packaging
(Continued)

body and comes into contact with the absorbent articles. The surface of the packaging sheet has a plurality of surface recesses formed so as to be recessed toward the back surface side and the back surface of the packaging sheet has a plurality of back surface recesses formed so as to be recessed toward the surface.

23 Claims, 13 Drawing Sheets

(58) Field of Classification Search
USPC .......................................................... 206/494
See application file for complete search history.

(56) References Cited

U.S. PATENT DOCUMENTS

| | | | | |
|---|---|---|---|---|
| 7,938,581 | B2* | 5/2011 | Ping .................. | B65D 81/2038 383/100 |
| 2005/0281489 | A1* | 12/2005 | Yeh ..................... | B65D 33/007 383/35 |
| 2007/0175789 | A1* | 8/2007 | Ronnberg ............ | A61F 15/001 206/494 |
| 2008/0000793 | A1* | 1/2008 | Messerschmidt ..... | A61F 15/001 206/459.5 |
| 2008/0087569 | A1* | 4/2008 | Ponomarenko ....... | A61F 13/495 206/570 |
| 2008/0260996 | A1* | 10/2008 | Heilman ............... | A61Q 19/00 428/141 |
| 2009/0084698 | A1* | 4/2009 | Ito ......................... | B65D 81/30 206/438 |
| 2009/0094945 | A1* | 4/2009 | Nakagawa ............ | B65B 61/025 53/451 |
| 2010/0098354 | A1* | 4/2010 | Fraser .................... | B31B 50/26 383/72 |
| 2011/0073513 | A1* | 3/2011 | Weisman ............. | A61F 13/15203 206/494 |
| 2011/0164835 | A1* | 7/2011 | Saggar ................. | B65D 33/004 383/105 |
| 2013/0098795 | A1* | 4/2013 | Biber ................... | A61F 13/5511 206/494 |
| 2014/0272223 | A1* | 9/2014 | Cheng .................. | D04H 1/4291 428/36.1 |
| 2015/0266663 | A1* | 9/2015 | Joseph ................. | B65D 85/62 206/526 |
| 2016/0107826 | A1* | 4/2016 | Motsch ................. | B65D 75/52 383/120 |
| 2018/0118438 | A1* | 5/2018 | Yamamoto ............. | B65B 61/18 |
| 2018/0228675 | A1* | 8/2018 | Hou ...................... | A61F 13/5638 |
| 2018/0289564 | A1* | 10/2018 | Sheehan ................. | B32B 27/34 |

FOREIGN PATENT DOCUMENTS

| | | |
|---|---|---|
| JP | 2000-51265 A | 2/2000 |
| JP | 3072476 U | 10/2000 |
| JP | 2009-536069 A | 10/2009 |
| JP | 2010-523424 A | 7/2010 |
| JP | 2013-139294 A | 7/2013 |
| JP | 2013-151297 A | 8/2013 |
| JP | 2015-73775 A | 4/2015 |
| WO | 2007/132434 A1 | 11/2007 |
| WO | 2013/085028 A1 | 6/2013 |

OTHER PUBLICATIONS

Office Action in CN Application No. 201780065591.2, dated Feb. 3, 2020, 16pp.
Office Action in JP Application No. 2016-208161, dated Sep. 24, 2019, 7pp.
Office Action in JP Application No. 2016-208162, dated Sep. 24, 2019, 7pp.
Office Action in JP Application No. 2016-208158, dated Oct. 1, 2019, 7pp.
International Search Report in PCT Application No. PCT/JP2017/037934, dated Dec. 26, 2017, 4pp.

* cited by examiner

PACKAGING BODY FOR ABSORBENT ARTICLE

RELATED APPLICATIONS

The present application is a national phase of International Application Number PCT/JP2017/037934, filed Oct. 20, 2017, which claims priority to JP2016-208158, filed Oct. 24, 2016, JP2016-208161, filed Oct. 24, 2016, and JP2016-208162, filed Oct. 24, 2016.

TECHNICAL FIELD

The present invention relates to a packaging body for an absorbent article for packaging an absorbent article.

BACKGROUND ART

Patent Literature 1 discloses a packaging body for packaging an absorbent article, wherein a packaging sheet constituting the packaging body is subjected to an embossing process. By embossing the packaging sheet, a matte effect is exhibited to obtain a high-grade sense (for example, see paragraphs 0005, 0050, and 0051 of Patent Literature 1).

In a packaging body for an absorbent article of Patent Literature 2, a wearer image representing a wearer of the absorbent article is provided on a bag-shaped packaging sheet for packaging the absorbent article. The wearer image of Patent Literature 2 is configured to have higher image quality than an assistant image representing an assistant of the wearer. According to the packaging body of Patent Literature 2, the wearer who is a target of the absorbent article can be intuitively recognized. In addition, the packaging body of Patent Literature 2 can display a state in which the assistant holds the wearer by providing the wearer image and the assistant image to improve a desire of purchase by reminding a user of a friendly image.

CITATION LIST

Patent Literature

Patent Literature 1: JP 2009-536069 A
Patent Literature 2: JP 2013-139294 A

SUMMARY OF INVENTION

Technical Problem

The packaging body of Patent Literature 1 is configured to increase a high grade sense of the packaging body and increase the desire of purchase of the user. In addition, the packaging body of Patent Literature 2 is configured to increase the desire of purchase of the user by reminding a friendly image while recognizing a target person of the absorbent article. In recent years, various packaging bodies as described above have been provided, but it is required to further attract attention of the user and to further increase the desire of purchase.

The present invention has been made in view of the above-mentioned problems, and an object of the present invention is to provide a packaging body for absorbent articles which can further attract an attention of a user and further increase a desire of purchase of the user.

Solution to Problem

A packaging body for absorbent articles (a packaging body 1) according to the present disclosure is a packaging body for absorbent articles including absorbent articles (absorbent articles 20) and a bag-shaped packaging sheet (a packaging sheet 10) that packages a plurality of absorbent articles, wherein the packaging sheet includes a surface (a surface 10T) that constitutes an outer surface of the packaging body, and a back surface (a back surface 10B) that constitutes an inner surface of the packaging body and comes into contact with the absorbent articles, the surface of the packaging sheet has a plurality of surface recesses (surface recesses 13) formed so as to be recessed toward the back surface side, and the back surface of the packaging sheet has a plurality of back surface recesses (back surface recesses 14) formed so as to be recessed toward the surface side.

A packaging body for absorbent articles (a packaging body 1X) according to another aspect of the present disclosure is a packaging body for absorbent articles including absorbent articles (absorbent articles 20) and a bag-shaped packaging sheet (a packaging sheet 10X) that packages a plurality of absorbent articles, wherein the packaging sheet includes a surface (a surface 10T) that constitutes an outer surface of the packaging body, and a back surface (a back surface 10B) that constitutes an inner surface of the packaging body and comes into contact with the absorbent articles, a plurality of surface recesses (surface recesses 13) which are recessed in a thickness direction of the packaging sheet are formed on the surface of the packaging sheet, a plurality of article recesses (sheet recesses 24) which are recessed in a thickness direction of the absorbent articles are formed on the outer surfaces of the absorbent articles, and the surface recesses are provided on regions overlapping the article recesses.

A packaging body for absorbent articles (a packaging body 1P) according to another aspect is a packaging body for absorbent articles including absorbent articles (absorbent articles 20) and a bag-shaped packaging sheet (a packaging sheet 10P) that packages a plurality of absorbent articles, wherein the packaging sheet includes a surface (a surface 10T) that constitutes an outer surface of the packaging body, and a back surface (a back surface 10B) that constitutes an inner surface of the packaging body and comes into contact with the absorbent articles, a plurality of packaging recesses (surface recesses 13) which are recessed toward the back surface side and a wearer image (a wearer image 15) representing a wearer of the absorbent articles are provided on the surface of the packaging sheet, and the packaging recesses are irregularly disposed in a region in which the wearer image is provided.

DESCRIPTION OF EMBODIMENTS

Figure 1:
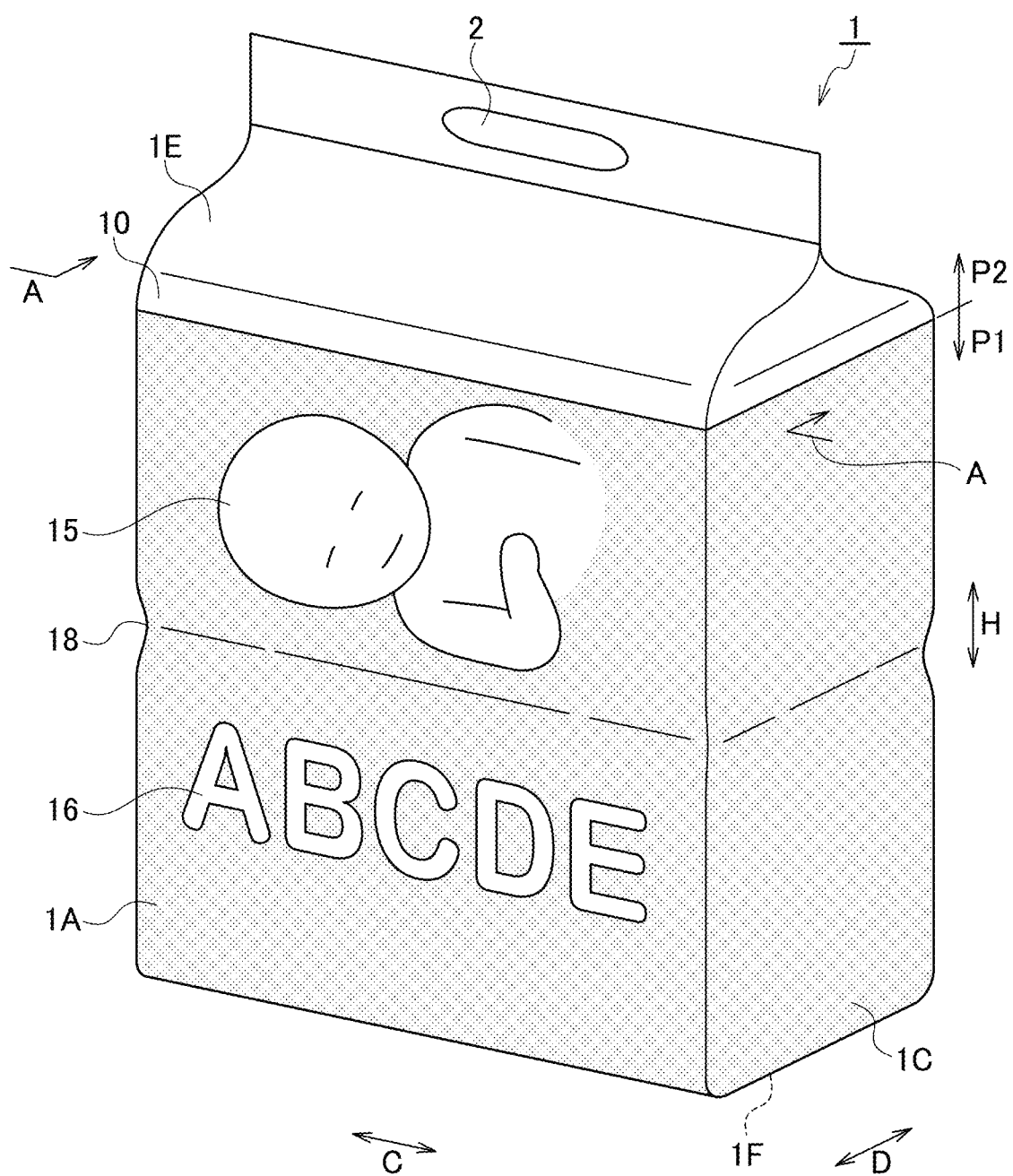
FIG. 1 is a perspective view of a front side of a packaging body for an absorbent article according to a first embodiment.

At least the following matters will become apparent from the description of the present specification and the accompanying drawings.

A packaging body for absorbent articles includes absorbent articles and a bag-shaped packaging sheet that packages a plurality of absorbent articles, the packaging sheet includes a surface that constitutes an outer surface of the packaging body, and a back surface that constitutes an inner surface of the packaging body and comes into contact with the absorbent articles, the surface of the packaging sheet has a plurality of surface recesses formed so as to be recessed toward the back surface side, and the back surface of the packaging sheet has a plurality of back surface recesses formed so as to be recessed toward the surface side.

Since the surface of the packaging sheet has the surface recesses formed thereon, a finger of a user is caught on the surface recesses when the user grasps the packaging body. Since it becomes more difficult for the finger to slide on the outer surface of the packaging body, the user can easily transport the packaging body for absorbent articles.

Since the back surface recesses are formed on the back surface of the packaging sheet, the back surface recesses come into contact with the absorbent articles and the absorbent articles are caught on the back surface recesses. Since it becomes more difficult for the absorbent articles to slide on the inner surface of the packaging body, it is possible to suppress a displacement of the absorbent articles in an unopened state. In addition, in a state in which the number of absorbent articles is reduced after opening, a space occurs in the packaging body and an alignment state of the absorbent articles is broken. The alignment state of the absorbent articles can be maintained by the fact that it is difficult for the absorbent articles to slide on the inner surface of the packaging body. Therefore, functionality at the time of use, such as ease of transportation of the packaging body and maintenance of the alignment state of the absorbent articles after opening the packaging body can be increased. By increasing the functionality at the time of use, a desire of purchase of the user can be further increased by further increasing an attention of the user.

In addition, since the plurality of surface recesses are formed on the surface of the packaging sheet, light incident on a region in which the surface recesses are provided and light incident on a region in which the surface recesses are not provided are reflected in different modes. The light incident on the surface of the packaging sheet becomes a complex reflection mode and aesthetics can be increased. By increasing the aesthetics, a desire of purchase of the user can be further increased by further increasing an attention of the user.

In the packaging body for absorbent articles as described above, it is preferable that the absorbent articles include an exterior sheet disposed on the outer surfaces of the absorbent articles, and the exterior sheet is made of non-woven fabric and comes into contact with the back surface recesses of the above-mentioned packaging sheet.

When the packaging sheet comes into contact with the back surface recesses, the fiber of the exterior sheet are caught on the back surface recesses, and it becomes more difficult for the absorbent articles to slide on the inner surface of the packaging body.

In the packaging body for absorbent articles as described above, it is preferable that the exterior sheet has a plurality of sheet projections protruding in a thickness direction of the absorbent article and sheet recesses disposed between the sheet projections, and the sheet projections and the sheet recesses come into contact with the back surface recesses, respectively.

The sheet recesses and the sheet projections are caught on the back surface recesses and it becomes more difficult for the absorbent articles to slide on the inner surface of the packaging body.

In the packaging body for absorbent articles as described above, it is preferable that the packaging body includes laminate members in which the absorbent articles are laminated in a thickness direction, the laminate members are laminated in an orthogonal direction orthogonal to the thickness direction, the packaging sheet is formed with constricted portions which are recessed toward the back surface side, and the constricted portions are formed along a boundary between the laminate members.

Since the constricted portions are formed on the packaging body, the user can hook his or her finger to the constricted portions, which makes it easy to transport. In addition, since the back surface recesses of the packaging sheet are caught on the outer surface of the absorbent article, it is easy to maintain a shape of the constricted portion which is recessed toward the absorbent article side. By maintaining the shape of the constricted portion, the user can easily grasp a portion at which the user hooks his/her finger or the like at the time of transportation, so that the functionality at the time of use can be further improved.

Since the constricted portions are formed along the boundary between the laminate members, a deformation of upper stage laminate members is difficult to be transferred to lower stage laminate members even if an alignment state of the upper stage laminate members is broken, and it is easy to maintain an aligned state of the lower stage laminate members. Therefore, it is easier to maintain the alignment state of the absorbent articles.

In the packaging body for absorbent articles as described above, it is preferable that the packaging sheet includes a film layer and a printing layer provided on a surface side of the film layer, the surface recesses are formed on the film layer and the printing layer, and a depth of the surface recess of the film layer is shallower than the depth of the back surface recess of the film layer.

When a printing is performed on the packaging sheet, the printing layer can be provided on the film layer after forming the surface recesses and the back surface recesses on the film layer. In this case, since the depth of the surface recess is relatively shallow, it is easy to form the printing layer on the entire film layer without stains. By forming the printing layer without stains, the aesthetics of the packaging sheet can be further increased.

In the packaging body for absorbent articles as described above, it is preferable that a width of the surface recess and a width of the back surface recess are 0.15 mm or more and 2.0 mm or less, respectively, and an interval between the surface recesses and an interval between the back surface recesses are 0.15 mm or more and 2.0 mm or less, respectively.

According to such a configuration, the aesthetics can be increased and the functionality at the time of use, such as ease of transportation of the packaging body and maintenance of the alignment state of the absorbent articles after opening the packaging body can be further increased. In particular, since the plurality of surface recesses are in contact with the plurality of surface recesses when the packaging sheet is in contact with the finger, the ease of transporting the packaging body for absorbent articles can be further improved.

In the packaging body for absorbent articles as described above, it is preferable that the surface recesses and the back surface recesses are formed by embossing, an embossing rate of the surface recesses is 10% or more and 80% or less, and an embossing rate of the back surface recesses is 20% or more and 90% or less.

According to such a configuration, the aesthetics can be increased across the entirety of the packaging body and the functionality at the time of use, such as ease of transportation of the packaging body or ease of maintenance of the absorbent articles after opening the packaging body can be further increased.

In the packaging body for absorbent articles as described above, it is preferable that the packaging sheet has a perforation to form an extraction opening of the absorbent article, and the surface recesses and the back surface recesses cross the perforation.

In regions in which the surface recesses are provided and regions in which the back surface recesses are provided, tear strength of the perforation is different because positions of the recesses or the thickness of the packaging sheet are different. Since the surface recesses and the back surface recesses cross the perforation, it is difficult for the perforation to be tore at one time due to a change in the tear strength when the perforation is continuously opened. For this reason, it is possible to suppress an inadvertent increase of the extraction opening and to improve the functionality at the time of use.

In the packaging body for absorbent articles as described above, it is preferable that a mean deviation (MMD) of a surface friction coefficient of the surface of the packaging sheet is 0.0056 or more and 0.0257 or less, a mean deviation (MMD) of a surface friction coefficient of the back surface of the packaging sheet is 0.0061 or more and 0.0258 or less, a mean deviation (SMD) of surface roughness of the surface of the packaging sheet is 0.8504 or more and 4.4314 or less, and a mean deviation (SMD) of surface roughness of the back surface of the packaging sheet is 1.0942 or more and 3.4088 or less.

According to such a configuration, the aesthetics can be increased across the entirety of the packaging body and the functionality at the time of use, such as ease of transportation of the packaging body or ease of maintenance of the absorbent articles after opening the packaging body can be further increased.

A packaging body for absorbent articles includes absorbent articles and a bag-shaped packaging sheet that packages a plurality of absorbent articles, the packaging sheet includes a surface that constitutes an outer surface of the packaging body, and a back surface that constitutes an inner surface of the packaging body and comes into contact with outer surfaces of the absorbent articles, a plurality of surface recesses which are recessed in a thickness direction of the packaging sheet are formed on the surface of the packaging sheet, a plurality of article recesses which are recessed in a thickness direction of the absorbent articles are formed on the outer surfaces of the absorbent articles, and the surface recesses are provided on regions overlapping the article recesses.

When the user presses the packaging body from the outer surface toward the inner surface side, the packaging sheet is deformed on the basis of the surface recesses. The deformation of the packaging sheet is transferred to the absorbent articles and the absorbent articles are deformed on the basis of the article recesses. Since a plurality of deformation starting points by the surface recesses are formed on the packaging sheet, the packaging sheet is susceptible to be flexibly deformed. Further, since a plurality of deformation starting points by the articles recesses are formed on the absorbent articles, the absorbent articles are susceptible to be flexibly deformed. Since the surface recesses and the article recesses are disposed to overlap with each other, a force directed from the outer surface to the inner surface side of the packaging body acts on both the surface recesses and the article recesses, and the packaging sheet and the absorbent articles are susceptible to be flexibly deformed together. Since the packaging body is greatly deformed with a relatively small force when the user pushes the packaging body from the outer surface toward the inner surface side, the user can feel softness of the absorbent articles or recall a soft image thereof. The user recognizes the fact that the absorbent articles are the absorbent articles which are soft and mild to a skin, so that the desire of purchase can be increased.

In the packaging body for absorbent articles as described above, it is preferable that a plurality of back surface recesses which are recessed in a thickness direction of the packaging sheet are formed on the back surface of the packaging sheet, and a depth of the surface recess is shallower than a depth of the back surface recess.

Since the depth of the surface recess is relatively shallow, a contact area between a finger and a surface of the packaging sheet can be secured to be widened when the finger of the user is in contact with the surface of the packaging sheet. For this reason, a force pressed by the user is more easily transferred to the packaging sheet and the absorbent articles, so that flexible deformation of the packaging sheet and the absorbent articles can be realized. In addition, since the depth of the back surface recess is relatively deep, the contact area between the absorbent article and the back surface of the packaging sheet tends to be small. The contact area between the absorbent article and the back surface of the packaging sheet is small so that when the force is transferred to the absorbent article through the packaging sheet, an action point of the force is reduced and the force is concentrated on the action point. Therefore, the packaging sheet and the absorbent article are easily deformed more flexibly, and it is easy for the user to recognize that the absorbent articles are the absorbent articles which are soft and mild to a skin.

In the packaging body for absorbent articles as described above, it is preferable that the packaging sheet is constituted by a film, the outer surface of the absorbent article is constituted by a nonwoven fabric, and an interval between the surface recesses is shorter than an interval between the article recesses.

In the packaging sheet made of a film, the more the surface recess is, the more the deformation starting point becomes, and it is easy to be deformed. Since the interval between the surface recesses is relatively short, it is easy to secure flexibility of the packaging sheet. Meanwhile, since the fibers of the nonwoven fabric are dense at a portion in which the article recess is formed, it is easy for the nonwoven fabric to become hard. For this reason, as the number of the article recesses increases, the nonwoven fabric is difficult to deform. Due to the relatively long interval between the article recesses, flexibility of the absorbent article can be easily secured. Therefore, the packaging sheet and the absorbent article are be easily deformed more flexibly, and it is easy for the user to recognize that the absorbent articles are the absorbent articles which are soft and mild to a skin.

In addition, since the interval between the surface recesses is relatively shallow, the force tends to be easily transferred to the surface recesses when the user presses the outer surface of the packaging body, so that the packaging sheet is more easily deformed. Therefore, the user can feel softness of the absorbent articles or recall a soft image thereof.

In the packaging body for absorbent articles as described above, it is preferable that the packaging sheet has a perforation to form an extraction opening of the absorbent article, the surface recesses includes first portions extending in a direction along the perforation and second portions extending in a direction crossing the perforation, and the number of the second portions in a region in which the perforation is provided is greater than the number of the first portions.

The tear strength of the perforation is different in a portion in which the surface recesses are formed and a portion in which the surface recesses are not formed. Since the number of the second portions is relatively great in the region in which the perforation is provided, a point at which the tear strength of the perforation changes is increased and it is difficult for the perforation to be tore at one time. For this reason, it is possible to suppress an inadvertent increase of the extraction opening.

Since a thickness is different between the portion in which the surface recesses are formed and the portion in which the surface recesses are not formed, a sound generated at the time of breaking of the perforation differs. For this reason, if the surface recesses are disposed in parallel to the perforation, a frequency of the sound generated at the time of breaking of the perforation is constant, and it is easy to feel the sound greatly. Meanwhile, if the surface recesses cross the perforation, the frequency of the sound generated at the time of breaking of the perforation is dispersed, and it is easy to feel the sound small.

In the packaging body for absorbent articles as described above, it is preferable that a bending stiffness of the packaging sheet is lower than the bending stiffness of the absorbent article.

Since the bending stiffness of the packaging sheet is relatively low, the packaging sheet is easily deformed when the user presses the packaging sheet, and the absorbent article is more easily deformed through the packaging sheet. Therefore, it is easy for the user to recognize that the absorbent articles are the absorbent articles which are soft and mild to a skin, so that the desire of purchase of the user can be increased.

In the packaging body for absorbent articles as described above, it is preferable that a width of the surface recess is 0.15 mm or more and 2.0 mm or less, an interval between the surface recesses is 0.15 mm or more and 2.0 mm or less, a width of the article recess is 0.25 mm or more and 5.0 mm or less, and an interval between the article recesses is 0.5 mm or more and 20.0 mm or less.

According to such a configuration, it is easy for the packaging sheet and the absorbent articles to be flexibly further deformed together. It is easy for the user to recognize that the absorbent articles are the absorbent articles which are soft and mild to a skin, so that the desire of purchase of the user can be further increased.

In the packaging body for absorbent articles as described above, it is preferable that the surface recesses and the article recesses are formed by embossing, an embossing rate of the surface recesses is 10% or more and 80% or less, and an embossing rate of the article recesses is 1% or more and 90% or less.

According to such a configuration, it is easy for the packaging sheet and the absorbent articles to be flexibly further deformed together. It is easy for the user to recognize that the absorbent articles are the absorbent articles which are soft and mild to a skin, so that the desire of purchase of the user can be further increased.

In the packaging body for absorbent articles as described above, it is preferable that a firmness of the packaging sheet is 46.3 mm or more and 52.4 mm or less, the bending stiffness of the packaging sheet is $0.064 \times 10^{-4}$ Nm/m or more and $0.077 \times 10^{-4}$ Nm/m or less, and a bending hysteresis of the packaging sheet is $0.030 \times 10^{-4}$ Nm/m or more and $0.007 \times 10^{-4}$ Nm/m or less.

According to such a configuration, the packaging sheet is more easily deformed. It is easy for the user to recognize that the absorbent articles are the absorbent articles which are soft and mild to a skin, so that the desire of purchase of the user can be further increased.

A packaging body for absorbent articles includes absorbent articles and a bag-shaped packaging sheet that packages a plurality of absorbent articles, the packaging sheet includes a surface that constitutes an outer surface of the packaging body, and a back surface that constitutes an inner surface of the packaging body and comes into contact with the absorbent articles, a plurality of packaging recesses which are recessed toward the back surface side and a wearer image representing a wearer of the absorbent articles are provided on the surface of the packaging sheet, and the packaging recesses are irregularly disposed in a region in which the wearer image is provided.

Since the packaging recesses are provided to be overlapped with the wearer image, light incident on the packaging sheet is diffusely reflected compared with a smooth packaging sheet, and the wearer image can be stereoscopically displayed. In addition, since convexoconcaves are formed by the packaging recesses in the wearer image, a depth feeling occurs and the wearer image can be stereoscopically displayed. Further, in general, a skin texture (skin) of a person is not a regular dot or line shape but an irregular shape. Since the packaging recesses are irregularly disposed, a skin-like texture can be given to the wearer image. By increasing the texture of the wearer image, the desire of purchase of the user can be further increased by further increasing an attention of the user.

In the packaging body for absorbent articles as described above, it is preferable that the packaging recesses include vertical portions along a vertical direction of a face of the wearer image and orthogonal portions along a direction orthogonal to the vertical directions, and the packaging recesses are curved shapes having the vertical portions and the orthogonal portions.

In general, the skin texture does not extend in a certain direction but extends in various directions. In addition, the skin texture is not a straight line shape but a curved line shape. Since the packaging recesses are the curved shapes having the vertical portions and the orthogonal portions, the packaging recesses can more exhibit visual effects such as the skin texture, and the texture of the wearer image can be further improved.

In the packaging body for absorbent articles as described above, it is preferable that the wearer image has shadow portions indicating shadows due to the convexoconcaves of the face, and the packaging recesses are provided in regions overlapping the shadow portions.

The face of the person is three-dimensional, and the shadows appear around, for example, a nasolabial fold, inner corners of eyes, eyebrows, and nose. Since the packaging recesses are formed in the shadow portions indicating the shadows of the wearer image, the shadows due to the convexoconcave shapes of the packaging recesses occur and a stereoscopic effect of the wearer image can be increased.

In the packaging body for absorbent articles as described above, it is preferable that an interval between the packaging recesses is 0.1 mm or more and 1.0 mm or less.

In general, an interval between the skin textures is often 0.1 mm or more and 1.0 mm or less. By setting the interval between the packaging recesses to 0.1 mm or more and 1.0 mm or less, the texture such as the skin can be represented and the texture of the wearer image can be increased.

In the packaging body for absorbent articles as described above, it is preferable that the packaging sheet includes a film layer and a printing layer provided on a surface side of the film layer, the back surface of the packaging sheet has back surface recesses formed so as to be recessed toward the surface side, the packaging recesses are formed on the film layer and the printing layer, and a depth of the packaging recess of the film layer is shallower than the depth of the back surface recess of the film layer.

When a printing is performed on the packaging sheet, the printing layer can be provided on the film layer after forming the packaging recesses on the film layer. In this case, since the depth of the packaging recess is relatively shallow, it is easy to form the printing layer on the entire film layer without stains. By forming the printing layer without stains, an image quality of the wearer image can be improved and the texture of the wearer image can be increased.

In the packaging body for absorbent articles as described above, it is preferable that the packaging sheet includes a printing region having the film layer and the printing layer, and a non-printing region that has the film layer and does not have the printing layer, the wearer image is provided in the printing region, and a depth of the packaging recess in the printing region is shallower than the depth of the packaging recess in the non-printing region.

Since the depth of the packaging recess in the printing region and the depth of the packaging recess in the non-printing region are different from each other, a reflection state of light differs between the printing region and the non-printing region. Since it is more visible than the packaging sheet of the flat surface and attracts the attention of the user, the desire of purchase of the user can be increased. In addition, since the depth of the packaging recess provided in the wearer image is relatively shallow, the texture of the wearer image can be smoothed. The texture such as the skin due to the diffused reflection of light can be obtained while maintaining the smoothness of the wearer image.

In the packaging body for absorbent articles as described above, it is preferable that a width of the packaging recess is 0.15 mm or more and 2.0 mm or less.

According to such a configuration, since it is easy for the packaging recesses to exhibit the visible effect such as the skin texture, the texture such as the skin can be given to the wearer image.

In the packaging body for absorbent articles as described above, it is preferable that the packaging recesses are formed by embossing, and an embossing rate of the packaging recesses is 10% or more and 80% or less.

According to such a configuration, the convexoconcaves due to the packaging recesses are provided on the entire packaging sheet, such that the wearer image can be more stereoscopically represented, and the texture such as the skin of the wearer image can be further increased.

In the packaging body for absorbent articles as described above, it is preferable that a firmness of the packaging sheet is 46.3 mm or more and 52.4 mm or less, the bending stiffness of the packaging sheet is $0.064 \times 10^{-4}$ Nm/m or more and $0.077 \times 10^{-4}$ Nm/m or less, and a bending hysteresis of the packaging sheet is $0.030 \times 10^{-4}$ Nm/m or more and $0.007 \times 10^{-4}$ Nm/m or less.

According to such a configuration, the packaging sheet is more easily deformed. Since the packaging sheet is flexibly deformed, the packaging sheet can exhibit a soft texture such as the skin and the texture such as the skin of the wearer image can be further increased.

===For Absorbent Articles According to Present Embodiment===

Hereinafter, a packaging body for absorbent articles according to first to third embodiments will be described with reference to the drawings. Further, in the following drawings, the same or similar parts are denoted by the same or similar reference symbols. It should be noted, however, that the drawings are schematic, and the ratios of the dimensions and the like are different from those of the real world. Therefore, specific dimensions and the like should be determined based on the following description. In addition, the drawings may include portions in which relationships or proportions of the dimensions are different from each other.

First Embodiment

Figure 2:
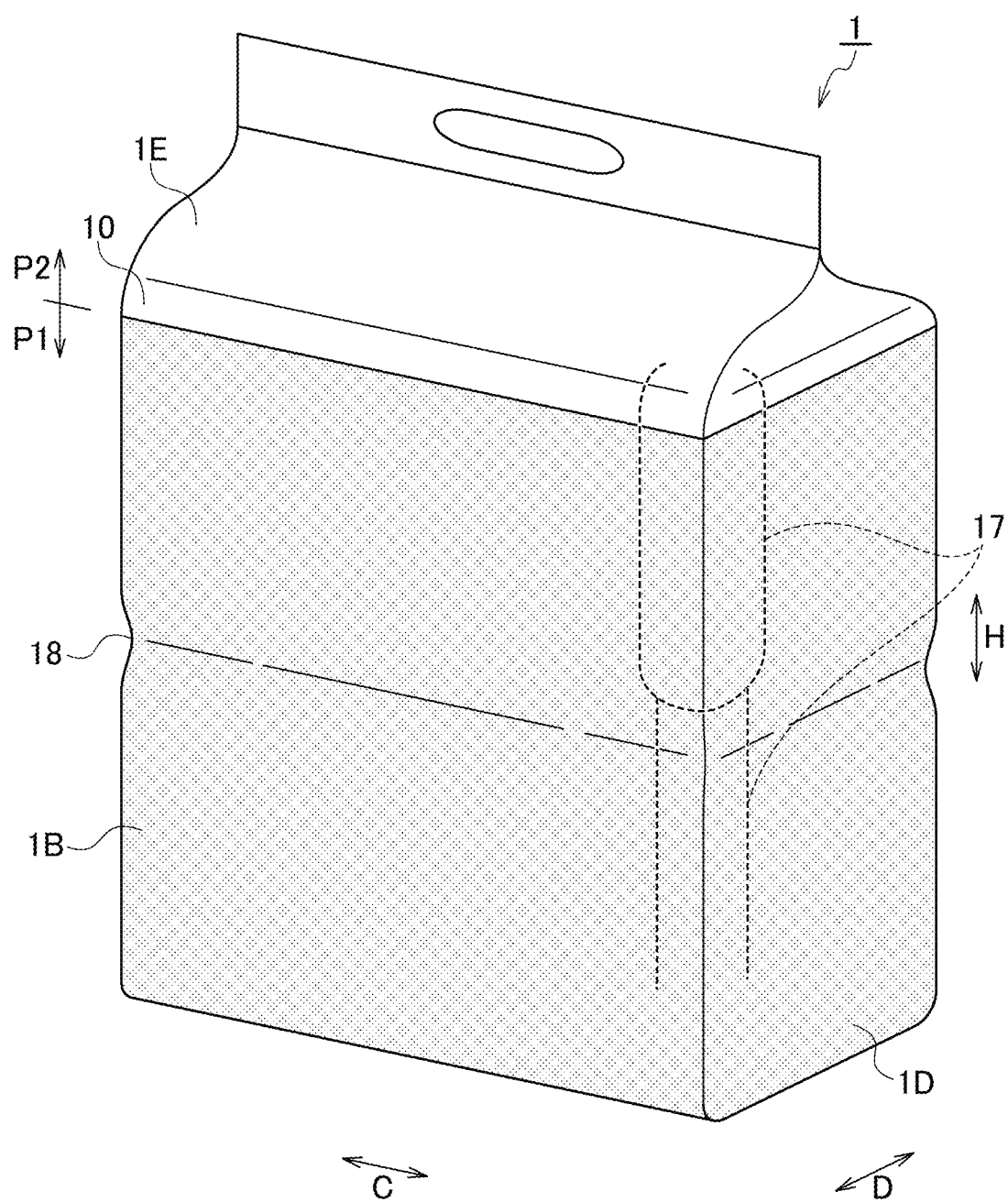
FIG. 2 is a perspective view of a back side of the packaging body for an absorbent article according to the first embodiment.
Figure 3:
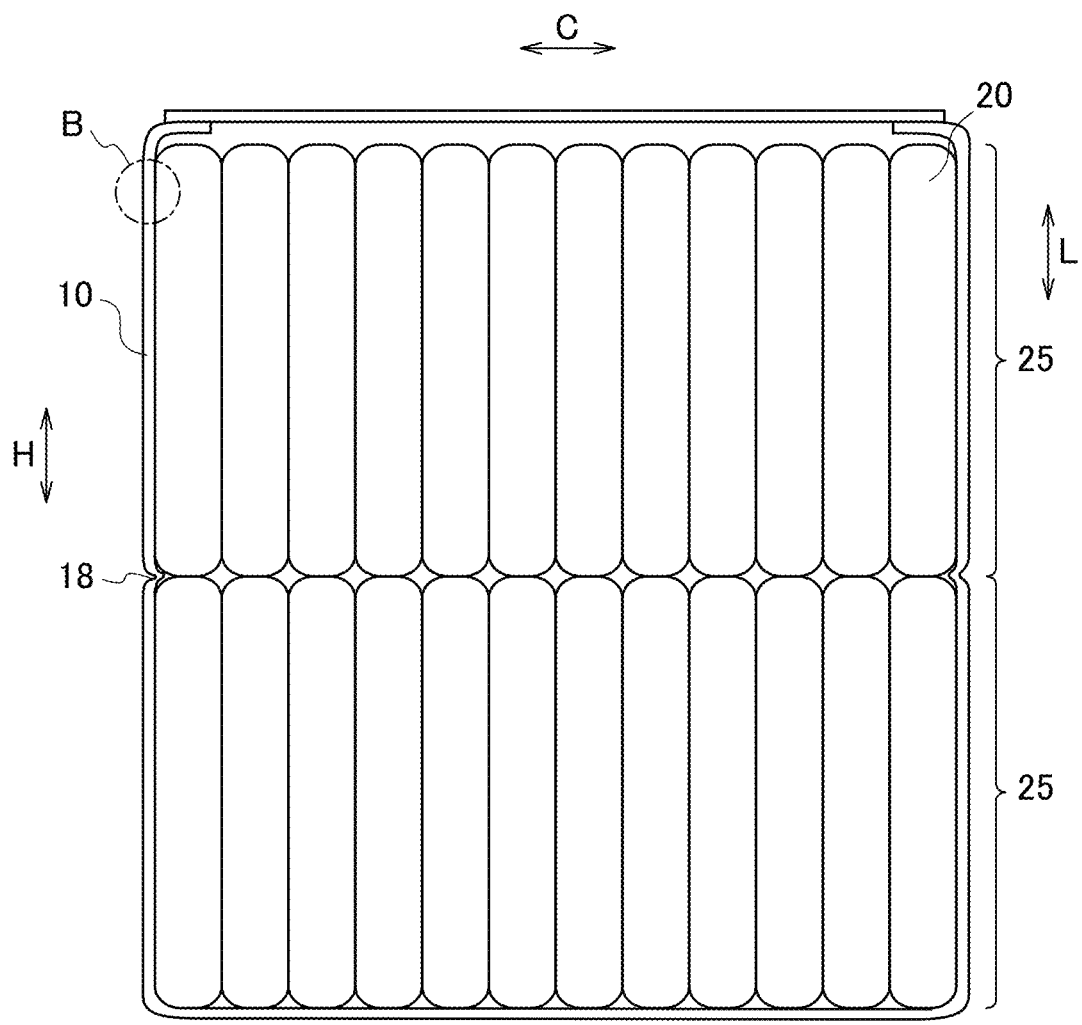
FIG. 3 is a cross-sectional view of the packaging body for an absorbent article taken along a line A-A illustrated in FIG. 1.
Figure 4:
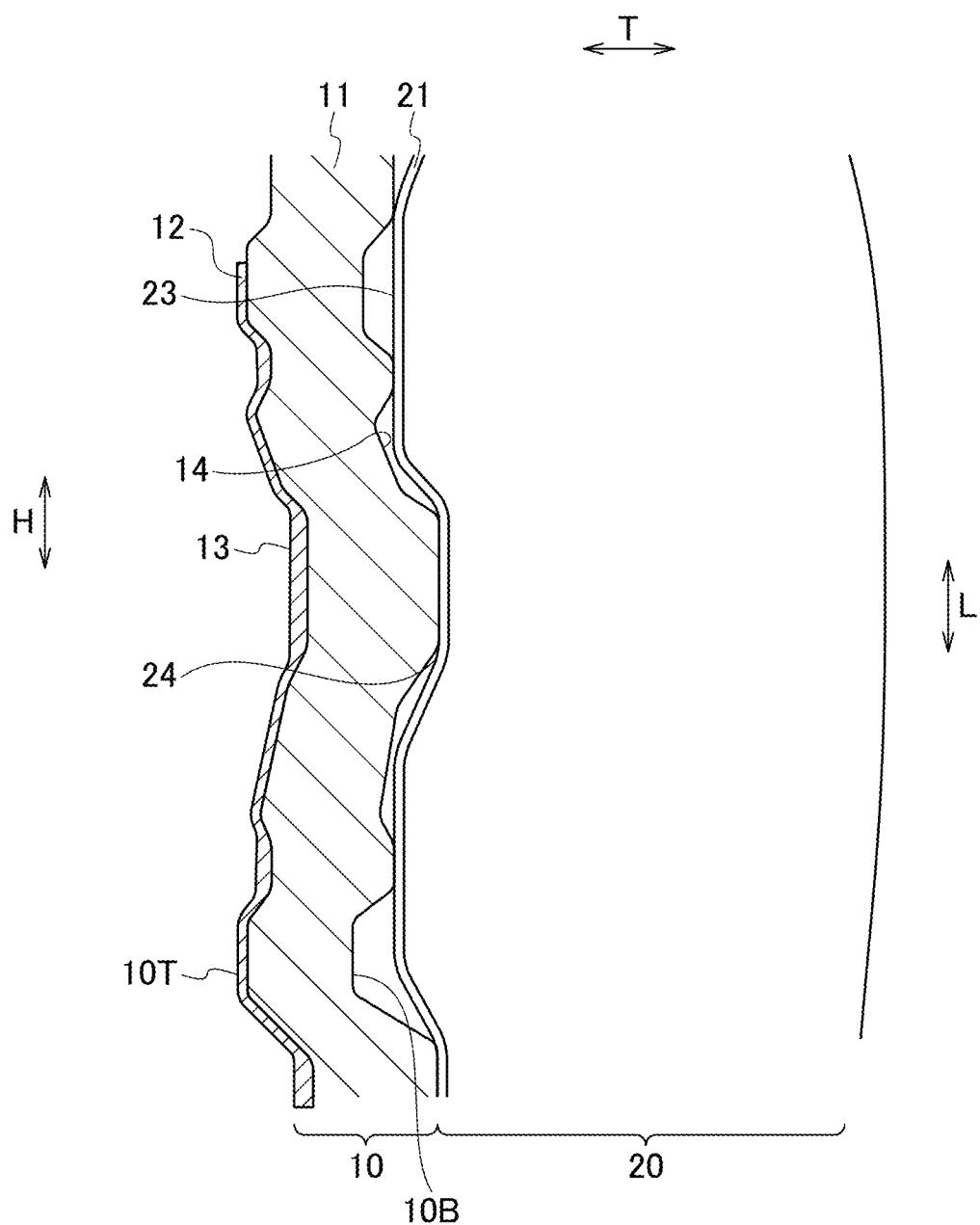
FIG. 4 is an enlarged view of a part B illustrated in FIG. 3.

FIG. 1 is a perspective view of a packaging body 1 for an absorbent article seen from a front side, FIG. 2 is a perspective view of the packaging body for an absorbent article seen from a back surface side, and FIG. 3 is a cross-sectional view of the packaging body for an absorbent article taken along a line A-A in FIG. 1. FIG. 4 is an enlarged view of a part B illustrated in FIG. 3. The packaging body 1 for absorbent articles (hereinafter referred to as the packaging body 1) includes absorbent articles 20 and a packaging sheet 10 for packaging a plurality of absorbent articles 20.

The packaging sheet 10 is formed in a bag shape. The plurality of absorbent articles 20 are accommodated in a space inside the packaging sheet 10. The packaging body 1 includes a front face 1A and a back face 1B opposing each other, a first side face 1C and a second side face 1D face which are connected to both the front face 1A and the back face 1B and oppose each other, a top face 1E located on an upper side in a displayed state, and a bottom face 1F located on a lower side in the displayed state. The top face 1E has a gripping part 2 formed so that the user holds his/her finger at the time of transportation. The packaging body 1 includes a height direction H extending vertically in the displayed state, a lateral direction C extending horizontally in the displayed state, and a depth direction D orthogonal to the height direction H and the lateral direction C.

As the absorbent article 20, for example, a disposable diaper, a sanitary napkin, and an absorbent pad can be exemplified. The absorbent article 20 according to the present embodiment is the disposable diaper, which is accommodated in the packaging sheet 10 in a state folded in two portions. The absorbent article 20 includes a thickness direction T, a longitudinal direction L along a front-back direction of the absorbent article 20, and a width direction orthogonal to the longitudinal direction L and the thickness direction T. The longitudinal direction L of the absorbent article 20 is along the height direction H of the packaging body 1, the width direction of the absorbent article 20 is along the depth direction D of the packaging body 1, and the thickness direction T of the absorbent article 20 is along the lateral direction C of the packaging body 1.

The packaging body 1 includes a plurality of laminate members 25, as illustrated in FIG. 3. The laminate member 25 is an assembly in which the absorbent articles 20 are laminated in the thickness direction T. The laminate members 25 are overlapped in the longitudinal direction L of the absorbent article 20 (the height direction H of the packaging body 1). Further, the laminate members 25 may be overlapped in the longitudinal direction L or the width direction which is orthogonal to the thickness direction T of the absorbent article 20, and may be overlapped in the width direction of the absorbent article 20 (the depth direction D of the packaging body 1). The plurality of laminate members 25 are adjacent to each other.

The absorbent article 20 has at least an absorber (not shown) and an exterior sheet 21 constituting an outer surface of the absorbent article 20. The exterior sheet 21 is, for example, a sheet disposed on a non-skin contact surface of the absorbent article 20. The exterior sheet 21 is constituted by a nonwoven fabric. Further, the exterior sheet 21 may be constituted by a film. The exterior sheet 21 includes a sheet projection 23 protruding in the thickness direction T of the absorbent article 20, and a sheet recess 24 which is recessed in the thickness direction T of the absorbent article 20. A boundary between the sheet projection 23 and the sheet recess 24 is a midpoint in the thickness direction of the exterior sheet 21. The sheet projection 23 and the sheet recess 24 are alternately disposed in the longitudinal direction L of the absorbent article 20 (the height direction H of the packaging body 1) and are extended in the width direction of the absorbent article 20 (the depth direction D of the packaging body 1). Further, the sheet projection 23 and the sheet recess 24 may be irregularly disposed, and may be alternately disposed in the width direction of the absorbent article and may be extended in the longitudinal direction L thereof. Further, the sheet projection 23 and the sheet recess 24 may be formed by embossing the exterior sheet 21 itself, and may be formed on the exterior sheet 21 by an influence of convexoconcave shapes formed on the absorber. A width of the sheet recess 24 may be 0.25 mm or more and 5.0 mm or less. An interval between the sheet recesses 24 may be 0.5 mm or more and 20.0 mm or less. In a form in which the width and the interval of the sheet recess are not constant, it is preferable that the width and the interval of all sheet recesses are within the numerical range.

The sheet recess 24 of the exterior sheet 21 is recessed in the thickness direction T of the absorbent article 20 on the outer surface of the absorbent article 20 to constitute the article recess according to the present invention. The article recess may be recessed in the thickness direction T on the outer surface of the absorbent article 20, may be a recess formed by embossing the exterior sheet 21 itself, and may be a recess formed on the exterior sheet 21 by an influence formed on the absorber itself. The sheet recess according to the present embodiment is formed by performing an embossing processing for the exterior sheet. An embossing rate of the article recess is 1% or more and 90% or less. The embossing rate is a ratio of an area of the sheet recess 24 per unit area.

Figure 5:
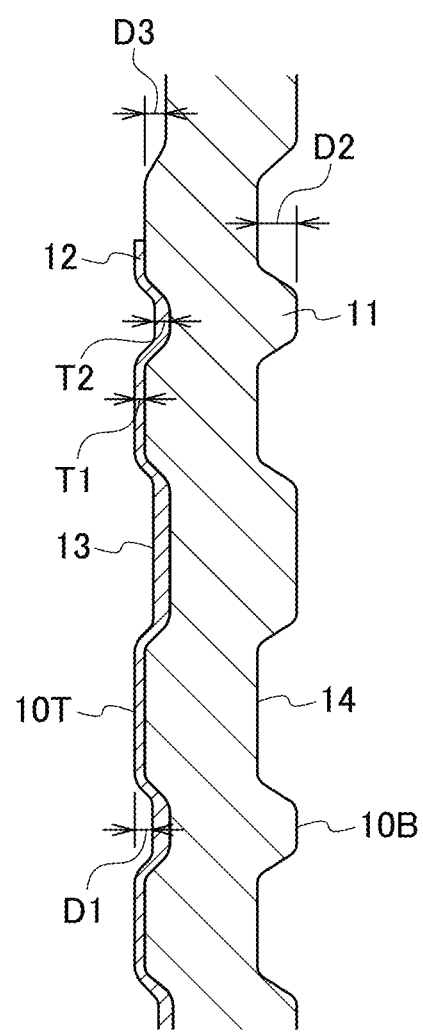
FIG. 5 is a cross-sectional view schematically illustrating a cross section of a packaging sheet according to the first embodiment.
Figure 6:
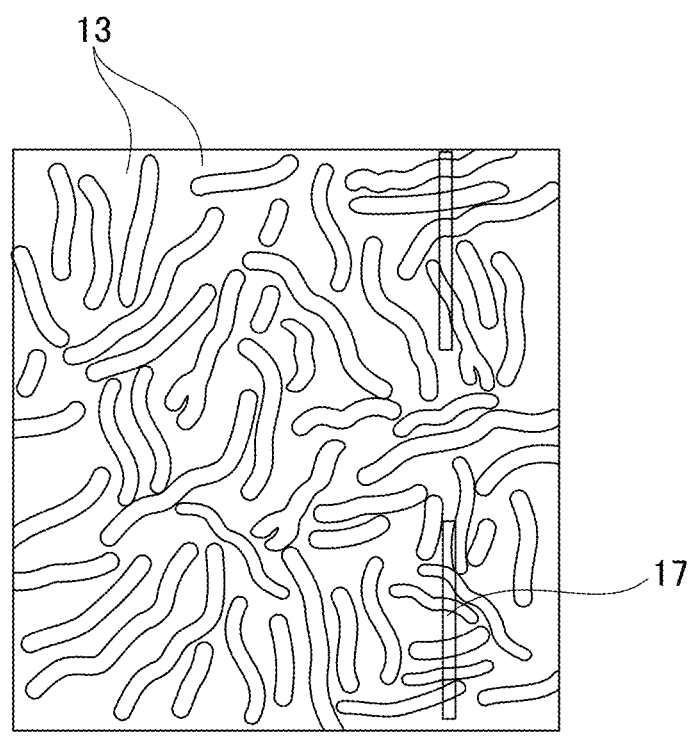
FIG. 6 is a plan view schematically illustrating a surface of the packaging sheet according to the first embodiment.

The packaging sheet 10 is formed of a film and is formed in a bag shape. FIG. 5 is a cross-sectional view schematically illustrating a cross section of the packaging sheet 10 and FIG. 6 is a plan view schematically illustrating a surface of the packaging sheet 10. A surface 10T of the packaging sheet 10 constitutes the outer surface of the packaging body 1, and a back surface 10B of the packaging sheet 10 constitutes an inner surface of the packaging body 1 and comes into contact with the absorbent article 20.

The packaging sheet 10 includes a film layer 11 and a printing layer 12 provided on a surface side of the film layer 11. The printing layer 12 according to the present embodiment is provided on the surface side of the film layer 11 and is not provided on a back surface side of the film layer 11. The printing layer 12 may be provided on the back surface side of the film layer 11. A thickness of the film layer 11 may be thinner than a thickness of the printing layer 12. The thickness of the printing layer 12 may be constant or may vary depending on the portion. Specifically, as illustrated in FIG. 5, a thickness T2 of the printing layer on the bottom face of the surface recess 13 can be thicker than a thickness T1 of the printing layer 12 on the top face of the surface recess. The printing layer 12 is provided on at least the front face 1A, the back face 1B, the first side face 1C, and the second side face 1D of the packaging body 1. In FIGS. 1 and 2, a printing region P1 in which the printing layer 12 is provided and a non-printing region P2 in which the printing layer 12 is not provided (which is formed by only the film layer 11) are illustrated. A wearer image 15 representing an image of a wearer and an identification image 16 displaying identification information such as a product name or the like, are provided in the printing region P1. The wearer image 15 is an image for indicating a target wearer, and includes a face of the target wearer and a part of a body thereof.

The packaging sheet 10 includes a perforation 17 forming an extraction opening of the absorbent article 20. As illustrated in FIG. 2, the perforation 17 extends over the back face 1B and the second side face 1D of the packaging body 1. The perforation 17 is constituted by an opening disposed in a dotted line shape and a region between the openings. The perforation 17 is continuous with a portion extending in the height direction H of the packaging body and a portion extending in the lateral direction C of the packaging body 1. The perforation 17 is broken at the time of use so that the extraction opening for extracting the absorbent article 20 from the packaging body 1 is formed.

A plurality of surface recesses 13 which are recessed toward the back surface 10B side of the packaging sheet 10 are formed on the surface 10T of the packaging sheet 10. A plurality of back surface recesses 14 which are recessed toward the surface 10T side of the packaging sheet 10 are formed on the back surface 10B of the packaging sheet 10. The surface recesses 13 and the back surface recesses 14 are portions depressed from the outermost surface to the inner surface side of the packaging sheet, and may be continuous or discontinuous. When the surface recesses 13 and the back surface recesses 14 are discontinuous, a distance in a direction of maximum in the depressed portion is defined as a length, and a distance in a direction orthogonal thereto is defined as a width. The surface recesses 13 and the back surface recesses 14 are irregularly disposed. The shape and arrangement of the surface recesses 13 and the back surface recesses 14 are not limited, may be, for example, a dot or a polygonal shape, may be a regular arrangement such as a zigzag shape or a grid-like dotted line shape, may be an irregular curved shape, may be an irregular straight line shape, or may be a combination thereof. The surface recesses 13 and the back surface recesses 14 are alternately disposed when viewed in plan. Specifically, the surface recesses 13 overlap regions in which the back surface recesses 14 are not formed, and the back surface recesses 14 overlap with regions in which the surface recesses 13 are not formed. The surface recesses 13 and the back surface recesses 14 may partially overlap. The regions of the surface recesses 13 and the regions of the back surface recesses 14 are recessed regions than a midpoint between the surface and the back surface of the packaging sheet 10.

Since the surface recesses 13 are formed on the surface 10T of the packaging sheet 10, the finger of the user easily catches on the surface recesses 13 when the user grasps the packaging body 1. Since it becomes more difficult for the finger to slide on the outer surface of the packaging body 1, the user easily transport the packaging body 1. Since the back surface recesses are formed on the back surface 10B of the packaging sheet 10, the back surface recesses 14 come into contact with the absorbent article 20 and the absorbent article 20 is caught on the back surface recesses 14. Since it becomes difficult for the absorbent articles to slide on the inner surface of the packaging body, it is possible to suppress a displacement of the absorbent articles 20 in an unopened state. The nonwoven fabric constituting the exterior sheet 21 comes into contact with the back surface recesses 14 of the packaging sheet 10, such that the fibers of the nonwoven fabric are caught on the back surface recesses 14 and it becomes more difficult for the absorbent articles 20 to slide on the inner surface of the packaging body 1. In addition, the sheet projection 23 and the sheet recess 24 of the exterior sheet 21 come into contact with the back surface recesses 14 of the packaging sheet 10, respectively. The sheet projection 23 and the sheet recess 24 are caught on the back surface recesses 14, such that it becomes more difficult for the absorbent articles 20 to slide on the back surface 10B of the packaging sheet 10.

In a state in which the number of absorbent articles 20 is reduced after opening, a space occurs in the packaging body 1 and an alignment state of the absorbent articles 20 is broken. The alignment state of the absorbent articles 20 can be maintained by the fact that it is difficult for the absorbent articles 20 to slide on the inner surface of the packaging body 1. Since the packaging body 1 includes the surface recesses 13 and the back surface recesses 14, functionality at the time of use, such as easiness of transportation of the packaging body 1 or maintenance of the alignment state of the absorbent articles 20 after opening the packaging body 1 can be increased and the desire of purchase of the user can be increased.

Since the plurality of surface recesses 13 are formed, light incident on a region on the surface 10T of the packaging sheet 10 in which the surface recesses are provided and light incident on a region in which the surface recesses are not provided are reflected in a different manner. The light incident on the surface 10T of the packaging sheet 10 becomes a complex reflection mode and aesthetics can be increased. Since the packaging sheet 10 differs from the packaging sheet made of only a flat surface in reflective mode of light, the packaging sheet 10 is more visible than the packaging sheet made of only the flat surface and attracts the attention of the user, thereby increasing the desire of purchase of the user.

A width of the surface recess 13 and a width of the back surface recess 14 are 0.15 mm or more and 2.0 mm or less, respectively. In a state in which the width of the surface recess 13 and the width of the back surface recess 14 are not constant, a maximum width may be 2.0 mm or less and a minimum width may be 0.15 mm or more. Preferably, the width of the surface recess may be 0.15 mm or more and 2.0 mm or less, and the width of the back surface recess may be 0.30 mm or more and 2.0 mm or less. More preferably, the width of the surface recess 13 and the width of the back surface recess 14 may be 0.3 mm or more and 0.5 mm or less that corresponds to an interval of ridges constituting a projection of a fingerprint. A length of the surface recess 13 is longer than the width of the surface recess 13, and a length of the back surface recess 14 is longer than the width of the back surface recess 14. Further, the length of the surface recess 13 may be the same as the width of the surface recess 13, and may be shorter than the width of the surface recess 13. The length of the back surface recess 14 may be the same as the width of the back surface recess 14, and may be shorter than the width of the back surface recess 14. An interval between the surface recesses 13 and an interval between the back surface recesses 14 are 0.15 mm or more and 2.0 mm or less, respectively. Preferably, the interval between the surface recesses may be 0.30 mm or more and 2.0 mm or less, and the interval between the back surface recesses may be 0.15 mm or more and 2.0 mm or less. More preferably, the interval may be 0.8 mm or less. By the surface recesses 13 and the back surface recesses 14 having such dimensions, the effect of increasing the aesthetics of the packaging body 1 and the effect of increasing the functionality at the time of use can be more easily obtained.

The surface recesses 13 are irregularly disposed on a region in which the wearer image 15 is provided. If regular surface recesses 13 are formed in the wearer image 15, a regular pattern is formed in the wearer image, and it is difficult to form the texture such as the skin. In general, the convexoconcaves on the surface of the skin of the person are not regular dot or line shapes but are irregularly formed. As the surface recesses 13 are irregularly formed, the texture of the skin of the wearer image can be further increased to increase aesthetics.

A depth D1 of the surface recess 13 is shallower than a depth D2 of the back surface recess 14. Since the surface recess 13 is formed on the printing layer 12 and the film layer 11, the depth D1 of the surface recess 13 herein is a depth in a state in which the printing layer 12 is provided on the film layer 11 and is a length in the thickness direction between the top face of the surface side of the printing layer 12 and the bottom face of the printing layer 12. The depth D2 of the back surface recess 14 is a distance in the thickness direction between the top face of the back surface side of the film layer 11 and the bottom face of the film layer 11. Since the depth D2 of the back surface recess 14 is relatively deep, the outer surface of the absorbent article 20 is easily caught on the back surface recess 14, such that the displacement or fall of the absorbent article 20 can be effectively suppressed.

In addition, a depth D3 of the surface recess 13 of the film layer 11 is shallower than the depth D2 of the back surface recess 14 of the film layer 11. The depth D3 of the surface recess 13 of the film layer 11 is a depth that does not include the printing layer 12, and is a distance in the thickness direction between the top face of the surface side of the film layer 11 and the bottom face of the film layer 11. When a printing is performed on the packaging sheet 10, the printing layer 12 can be provided on the film layer 11 after forming the surface recesses 13 and the back surface recesses 14 on the film layer 11. In this case, since the depth of the surface recess 13 is relatively shallow, it is easy to form the printing layer 12 on the entire film layer 11 without stains. By forming the printing layer 12 without stains, the aesthetics of the packaging sheet 10 can be further increased. The packaging sheet 10 is not entirely printed, but has a printing region P1 and a non-printing region P2. A depth of the surface recess 13 in the printing region P1 and a depth of the surface recess 13 in the non-printing region P2 are different, such that light incident on the printing region P1 and light incident on the non-printing region P2 are reflected in different modes. The light incident on the surface 10T of the packaging sheet 10 becomes a complex reflection mode and aesthetics can be increased.

The packaging sheet 10 according to the present embodiment can be acquired by performing the printing after embossing the film layer having a thickness of 0.04 mm to 0.20 mm. More preferably, the thickness of the film layer is 0.05 mm or more and 0.08 mm or less. The embossing is performed by passing the film layer 11 between a pair of rolls. The pair of rolls has a first roll having the projection corresponding to the back surface recess 14 provided on the outer peripheral surface thereof and a second roll having a flat outer peripheral surface. By passing the film layer 11 between the pair of rolls, the back surface recess 14 is formed by the projection of the first roll, and the film layer 11 is pulled along with the formation of the back surface recess 14, such that the projection is formed on the surface corresponding to the thickness direction of the back surface recess 14 and the surface recess 13 is formed in a region other than the back surface recess 14. The depth D2 of the back surface recess formed as described above is deeper than the depth D3 of the surface recess 13 of the film layer 11. Next, the printing is performed on the surface side of the film layer 11. A printing method is not particularly limited, and a flexo printing can be exemplified. The depth D2 of the back surface recess 14 is 50% or more of the thickness of the packaging sheet 10 and the depth D1 of the surface recess 13 is less than 50% of the thickness of the packaging sheet 10.

It is preferable that the depth D1 of the surface recess 13 is 10 μm to 50 μm, and it is preferable that the depth D2 of the back surface recess 14 is 40 μm to 70 μm. In order to form the printing layer 12 without stains, it is preferable that the depth of the surface recess 13 of the film layer 11 is less than 30 μm. In addition, generally, a size of a dirty is about 10 μm to 100 μm, and a size of a dust is about 30 μm. Since the depth of the surface recess is 10 μm to 50 μm, it is difficult for the entire garbage such as dirt or dust to enter the surface recess. In addition, since the depth of the surface recess 13 is equal to a size of the garbage, the garbage easily comes out from the surface recess 13 even if the garbage enters the surface recess 13, and it is possible to suppress the garbage from being continuously attached on the packaging sheet 10. In addition, since the depth of the surface recess 13 is shallower than the depth of the back surface recess 14, it is easy to exhibit an effect that it is difficult for the garbage to be attached on the surface of the packaging sheet 10.

An embossing rate of the surface recess 13 is 10% or more and 80% or less, and an embossing rate of the back surface recess 14 is 20% or more and 90% or less. The embossing rate is a ratio of an area of the surface recess 13 or the back surface recess 14 per unit area. By such an embossing rate, it is easier to obtain an effect of increasing aesthetics of the packaging body 1 and an effect of increasing functionality at the time of use. The packaging sheet 10 has the embossing, whereby the number of deformation starting points is increased and it is easy for the packaging sheet 10 to be flexibly deformed. Therefore, when the user presses the packaging sheet 10 with the finger, the packaging sheet 10 is attached around the finger such that a contact area between the finger and the packaging sheet 10 is increased. By increasing the contact area, frictional resistance between the finger and the packaging sheet 10 becomes large, and the user can easily transport the packaging body.

A mean deviation (MMD) of a surface friction coefficient of the surface 10T of the packaging sheet 10 may be 0.0056 or more and 0.0257 or less. A mean deviation (MMD) of a surface friction coefficient of the back surface 10B of the packaging sheet 10 may be 0.0061 or more and 0.0258 or less. A mean deviation (SMD) of a surface roughness of the surface 10T of the packaging sheet 10 may be 0.8504 or more and 4.4314 or less. A mean deviation (SMD) of a surface roughness of the back surface 10B of the packaging sheet 10 may be 1.0942 or more and 3.4088 or less. By the mean deviation (MMD) of the surface friction coefficient and the mean deviation (SMD) of the surface roughness described above, it is easier to obtain an effect of increasing aesthetics of the packaging body 1 and an effect of increasing functionality at the time of use.

The measurement of the mean deviation (MMD) of the surface friction coefficient and the mean deviation (SMD) of the surface roughness can be measured based on a characteristic value (References: Standardization and Analysis of Feel Evaluation (2nd edition), published by Kawabata, Sueo, Jul. 10, 1980) in KES manufactured by KATO TECH CO., Ltd. which is generally known as a characteristic value representing a feel of a sheet surface.

Specifically, the surface characteristics were measured by using KES-FB4 manufactured by KATO TECH Co., Ltd. and placing a specimen in a range of 1.0 to 1.0 cm in each sample on a test bed of a smooth metal plane. The surface roughness was measured by placing a load of 10 gf on the surface (or back surface) thereof and pressing a contact terminal having a width of 0.5 cm wound with a piano wire having a diameter of 0.5 mm on the sample, and the surface friction was measured by lining 10 piano wires which are the same as the contact terminal used for measuring the surface roughness, and pressing the contact surface to the specimen with a force of 50 fg by weight. In the measurement of surface friction and surface roughness, the specimen is moved 2 cm horizontally at a constant speed of 0.1 cm/sec, and a uniaxial tension of 20 gf/cm is given to the specimen. The mean deviation (MMD) of the surface friction coefficient and the mean deviation (SMD) [μm] of the surface roughness were obtained from the measurement results.

A firmness of the packaging sheet 10 may be 46.3 mm or more and 52.4 mm or less. According to such a packaging sheet, a drape property is improved and it is easy for the packaging sheet to be flexibly deformed. The bending stiffness of the packaging sheet 10 is $0.064 \times 10^{-4}$ Nm/m or more and $0.077 \times 10^{-4}$ Nm/m or less. According to such a packaging sheet, when the user presses the packaging sheet with the finger, it becomes easy for the packaging sheet to be easily deformed. The bending hysteresis (bending resiliency) of the packaging sheet 10 is $0.030 \times 10^{-4}$ Nm/m or more and $0.007 \times 10^{-4}$ Nm/m or less. According to such a packaging sheet, when the user presses the packaging sheet with the finger, it is easy for the deformation to be recovered. According to such a packaging sheet, when the garbage enters the surface recesses of the packaging sheet, the packaging sheet is flexibly deformed such that it is easy for the garbage to get out of the surface recesses and it is easy to exhibit an effect that it is difficult for the garbage to be attached on the surface of the packaging sheet.

The firmness of the packaging sheet is measured according to JIS L 1913 6.7.3. More specifically, five specimens of 38 mm×25 mm are taken, and the firmness was calculated from an average value of front sides and back sides after continuously measuring the front sides and back sides of the specimens with gurley tester (firmness tester No. 311 manufactured by YASUDA SEIKI SEISAKUSHO, Ltd.).

The bending stiffness of the packaging sheet 10 is measured by using KES FB-2 manufactured by KATO TECH CO., Ltd. A specimen with dimensions of 50 mm×100 mm is prepared, one end of the specimen in a longitudinal direction thereof is pinched in one of a pair of chucks, and the other end of the specimen in the longitudinal direction thereof is pinched in the other chuck. One of the chucks rotates about the other chuck, and the bending stiffness of the bent specimen is measured by a torque detector. Five sets of specimens are prepared, and an average value of the measured values is set to the bending stiffness.

The bending hysteresis of the packaging sheet is measured by the following sequence using "KES-FB2 AUTO-A" manufactured by KATO TECH CO., Ltd. as a use tool. The bending hysteresis is measured by setting the packaging sheet to an instrument, operating KES-EB2 AUTO-A according to an instruction manual supplied with the instrument, pushing a start switch to automatically clamp (firmly tight) it, and giving a predetermined curvature (a maximum curvature K=±2.5 cm−1). Three specimens are measured and an average value thereof is set to the bending hysteresis.

As illustrated in FIGS. 1 and 2, the constricted portion 18 which is recessed toward the back surface 10B side of the packaging sheet 10 (the inner surface side of the packaging body 1) is formed on the packaging sheet 10. The constricted portion 18 is formed along the boundary between the laminate members 25. The thickness of the absorbent article 20 of a folded state (a state in which the absorbent article 20 is accommodated in the packaging body 1) is not constant. A thickness of an end portion of the absorbent article 20 in the longitudinal direction L is smaller than a thickness of the center of the absorbent article 20 in the longitudinal direction L. A region having a small thickness of the absorbent article is laminated in the vicinity of the boundary of the laminate member 25. For this reason, the packaging sheet 10 is disposed along the outer surface of the absorbent article 20 to form the constricted portion 18.

Since the constricted portion 18 is formed on the packaging body 1, the user can hook his or her finger to the constricted portion 18, which makes it easy to transport the packaging body 1. In addition, when the user presses the constricted portion 18 with the finger, the finger squeezes into the constricted portion and a contact area between the finger and the packaging sheet 10 is increased. By increasing the contact area between the finger and the packaging sheet, a frictional coefficient between the finger and the packaging sheet becomes large, and the user can easily transport the packaging body. In addition, since the constricted portion 18 overlaps a region in which a thickness difference of the absorbent article occurs, it becomes easier for the user to hook the finger or the like on the portion in which the thickness difference occurs. In addition, since the back surface recesses 14 of the packaging sheet 10 are caught on the outer surface of the absorbent article 20, it is easy to maintain a shape of the constricted portion 18 which is recessed toward the absorbent article 20 side. By maintaining the shape of the constricted portion 18, the user can easily grasp a portion at which the user hooks his/her finger or the like at the time of transportation, so that the functionality at the time of use can be further improved.

Since the constricted portions are formed along the boundary between the laminate members 25, a deformation of upper stage laminate members 25 is difficult to be transferred to lower stage laminate members 25 even if an alignment state of the upper stage laminate members 25 is broken and it is easy to maintain an alignment state of the lower stage laminate members 25. Therefore, it becomes easier to maintain the alignment state of the absorbent articles.

The surface recesses 13 and the back surface recesses 14 cross the perforation 17 of the packaging sheet 10. At least portion of the surface recesses 13 and the back surface recesses 14 may cross the perforation 17, and a portion thereof may be disposed along the perforation 17. In regions in which the surface recesses 13 are provided and regions in which the back surface recesses 14 are provided, tear strength of the perforation 17 is different because positions of the recesses or the thickness of the packaging sheet are different. Since the surface recesses 13 and the back surface recesses 14 cross the perforation 17, it is difficult for the perforation 17 to be tore at one time due to a change in the tear strength when the perforation 17 is continuously opened. For this reason, it is possible to suppress an inadvertent increase of the extraction opening and to improve the functionality at the time of use.

Figure 7:
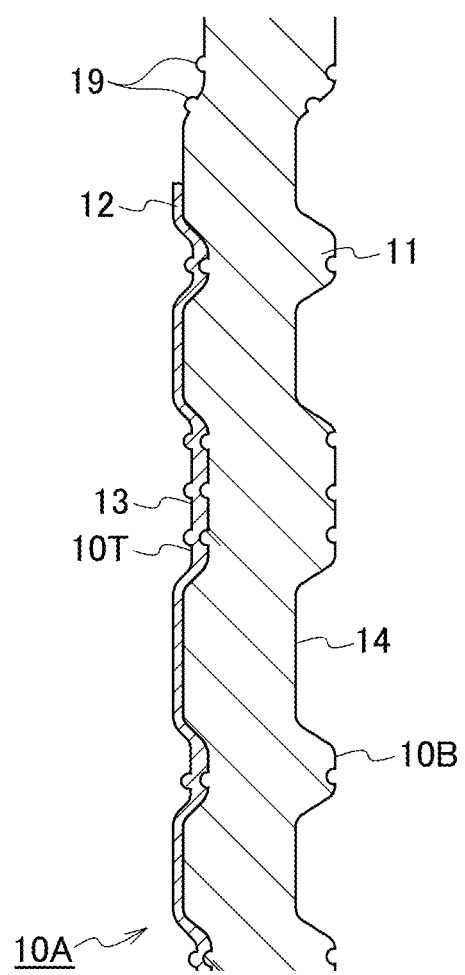
FIG. 7 is a cross-sectional view schematically illustrating a cross section of a packaging sheet according to a modified example.
Figure 8:
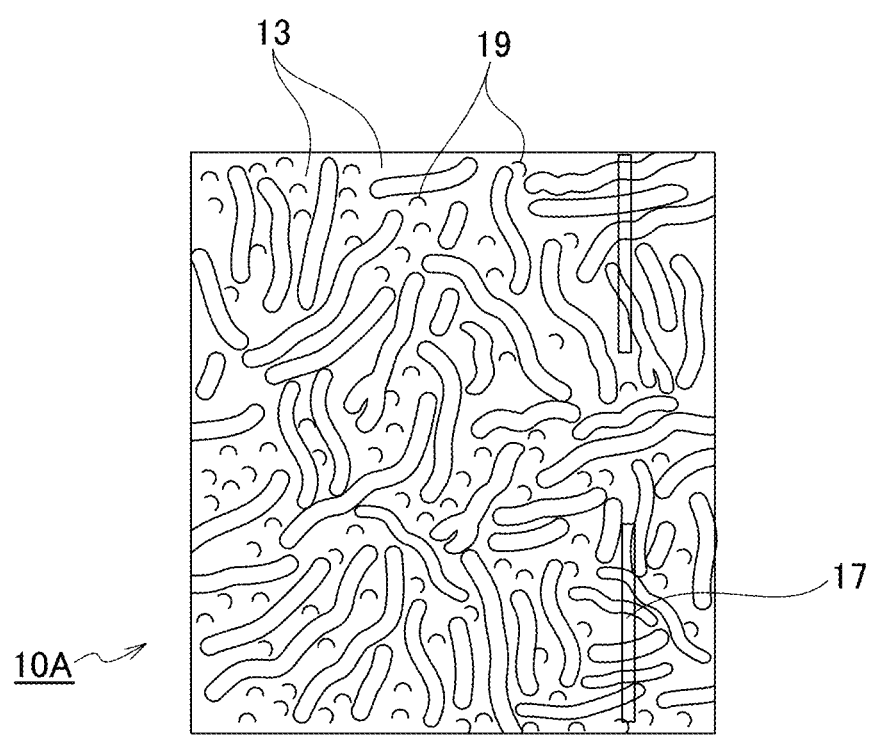
FIG. 8 is a plan view schematically illustrating a surface of the packaging sheet according to the modified example.

Next, a packaging sheet 10A according to a modified example in the first embodiment will be described with reference to FIGS. 7 and 8. FIG. 7 is a cross-sectional view of a packaging sheet according to a modified example and FIG. 8 is a plan view of the packaging sheet according to the modified example. Further, in the following description, the same components as those of the above-described embodiment are denoted by the same reference symbols and the description thereof is omitted. The packaging sheet 10A according to the modified example further has fine projections 19 formed on the surface and the back surface of the packaging sheet. The fine projections 19 have a convex shape protruding from the back surface side of the packaging sheet 10 to the surface side thereof. The fine projections 19 have an irregular curved shape, more specifically, a shape similar to an arc. The fine projections 19 are provided at positions that do not overlap with the back surface recesses 14 and overlap with the surface recesses 13. Further, the fine projections 19 may be provided at positions that overlap with the back surface recesses 14 and may be provided at positions that do not overlap with the surface recesses 13.

A width of the fine projection 19 is shorter than the width of the surface recess 13 and the width of the back surface recess 14, a length of the fine projection 19 is shorter than the length of the surface recess 13 and the length of the back surface recess 14, and a depth of the fine projection 19 is shallower than the depth of the surface recess 13 and the depth of the back surface recess 14. A ratio of dimensions of the fine projection 19 to dimensions (length, width, and depth) of the surface recess 13 and the back surface recess 14 may be 0.5 or less, and is more preferably 0.1 or less. It is preferable that the width of the fine projection 19 is 0.01 mm or more and 1.0 mm. It is preferable that a height of the fine projection 19 (a height from the bottom face of the surface recess 13 to an apex part of the fine projection) is 0.1 μm to 20 μm.

The fine projections 19 may be formed by blasting after the surface recesses 13 and the back surface recesses 14 are provided, may be formed before the surface recesses 13 and the back surface recesses 14 are provided, may be provided together with the surface recesses 13 and the back surface recesses 14 by providing projections corresponding to the fine projections 19 to a pair of rolls forming the surface recesses 13 and the back surface recesses 14, and may be formed together when the surface recesses 13 and the back surface recesses 14 are provided on the film layer 11. The fine projections 19 according to the modified example are formed by embossing. An embossing rate of the surface of the packaging sheet 10 including the fine projections 19 and the back surface recesses 14 is 80% or more.

Due to the fine projections 19 provided as described above, a matte effect exhibits and a high-grade sense can be obtained. In addition, in general, regions between the recesses constituting the skin texture of the person is not a smooth plane and have fine convexoconcaves formed therein. By providing the fine projections 19, the texture of the skin of the wearer image can be further increased to increase aesthetics. By providing the fine projections 19, it becomes more difficult for the surface 10T of the packaging sheet 10 to slide and it becomes easier to transport the packaging sheet 10. In addition, for example, if a matte processing by ink is carried out, garbage such as dust may be attached onto the packaging sheet because particles of the ink are fine. Since the fine projection 19 is larger than the particle of the ink, it is difficult for the garbage to be attached onto the packaging sheet. In addition, a contact area between the packaging sheet and the garbage is reduced by providing the fine projections, such that it becomes easy for the garbage attached onto the packaging sheet to be fallen off, and it is easy to exhibit an effect that it is difficult for the garbage to be attached onto the surface of the packaging sheet.

Second Embodiment

Figure 9:
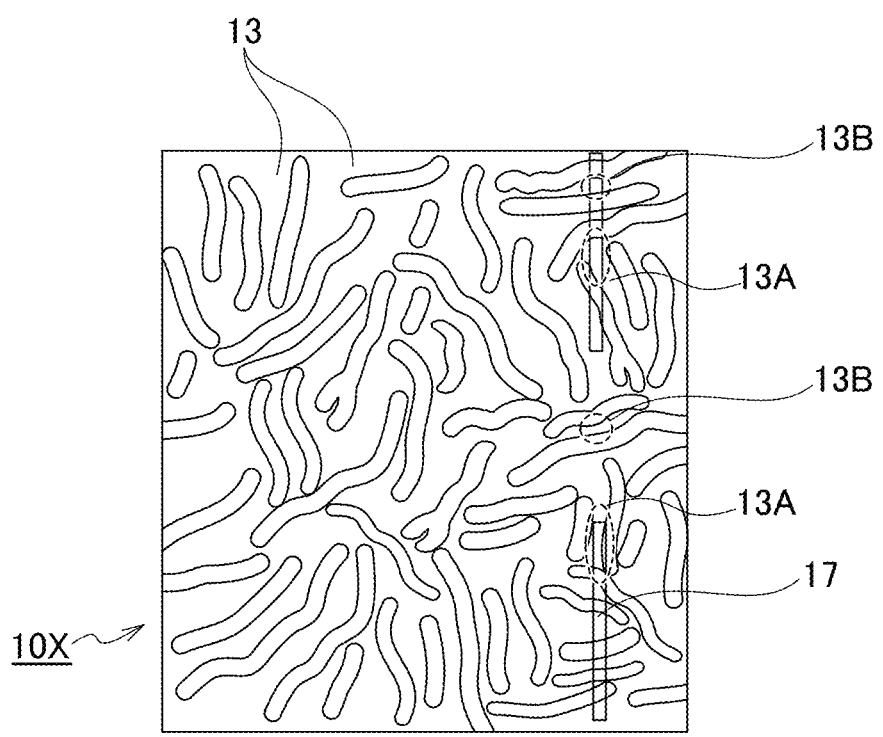
FIG. 9 is a plan view schematically illustrating a surface of a packaging sheet according to a second embodiment.

Next, a packaging body 1X for absorbent articles according to a second embodiment will be described. The overall structure of the packaging body according to the second embodiment is the same as that of the packaging body according to the first embodiment. FIGS. 1 to 5 and FIG. 7 also illustrate the packaging body according to the second embodiment. Reference symbol 1 in FIGS. 1 to 5 and FIG. 7 also denotes the packaging body 1X according to the second embodiment, reference symbol 10 in the drawings also denotes a packaging sheet 10X according to the second embodiment, and FIG. 9 is a plan view schematically illustrating a surface of the packaging sheet 10X according to the second embodiment.

The surface recesses 13 are provided in a region overlapping the sheet recesses 24 as the article recesses. At least a portion of the surface recesses is overlapped with the sheet recesses 24 in the thickness direction of the packaging sheet 10X. When the user presses the packaging body 1X from an outer surface of the packaging body 1X toward an inner surface, the packaging sheet 10X is deformed on the basis of the surface recesses 13. The deformation of the packaging sheet 10X is transferred to the absorbent article 20 such that the absorbent article 20 is deformed on the basis of the sheet recesses 24. Since a plurality of deformation starting points by the surface recesses 13 are formed on the packaging sheet 10X, the packaging sheet 10X is susceptible to be flexibly deformed. Further, since a plurality of deformation starting points by the sheet recesses 24 are formed on the absorbent articles 20, the absorbent articles 20 are susceptible to be flexibly deformed. Since the surface recesses 13 and the sheet recesses 24 are disposed to be overlapped with each other, a force directed from the outer surface to the inner surface side of the packaging body 1X acts on both the surface recesses 13 and the sheet recesses 24, and the packaging sheet 10X and the absorbent articles 20 are susceptible to be flexibly deformed together. Since the packaging body 1X is greatly deformed with a relatively small force when the user pushes the packaging body 1X from the outer surface toward the inner surface side, the user can feel softness of the absorbent articles 20 or recall a soft image thereof. The user recognizes the fact that the absorbent articles 20 are the absorbent articles which are soft and mild to a skin, so that the desire of purchase can be increased. In addition, since the back surface recesses 14 as well as the surface recesses 13 are provided, the number of the deformation starting points of the packaging sheet 10X is increased and the packaging sheet 10X is susceptible to be more deformed. Further, the surface recesses 13 may be formed on the packaging sheet 10X according to the second embodiment and the back surface recesses 14 may not be formed thereon.

A width of the surface recess 13 and a width of the back surface recess 14 are 0.15 mm or more and 2.0 mm or less, respectively. In a state in which the width of the surface recess 13 and the width of the back surface recess 14 are not constant, a maximum width may be 2.0 mm or less and a minimum width may be 0.15 mm or more. Preferably, the width of the surface recess may be 0.15 mm or more and 2.0 mm or less, and the width of the back surface recess may be 0.30 mm or more and 2.0 mm or less. More preferably, the width of the surface recess 13 and the width of the back surface recess 14 may be 0.3 mm or more and 0.5 mm or less that corresponds to an interval of ridges constituting a projection of a fingerprint. A length of the surface recess 13 is longer than the width of the surface recess 13, and a length of the back surface recess 14 is longer than the width of the back surface recess 14. Further, the length of the surface recess 13 may be the same as the width of the surface recess 13, and may be shorter than the width of the surface recess 13. The length of the back surface recess 14 may be the same as the width of the back surface recess 14, and may be shorter than the width of the back surface recess 14. An interval between the surface recesses 13 and an interval between the back surface recesses 14 are 0.15 mm or more and 2.0 mm or less, respectively. Preferably, the interval between the surface recesses may be 0.30 mm or more and 2.0 mm or less, and the interval between the back surface recesses may be 0.15 mm or more and 2.0 mm or less. More preferably, the interval may be 0.8 mm or less. By the surface recesses 13 and the back surface recesses 14 having such dimensions, it is easy for the packaging sheet and the absorbent articles to be flexibly further deformed together. It is easy for the user to recognize that the absorbent articles are the absorbent articles which are soft and mild to a skin, so that the desire of purchase of the user can be further increased.

In a state viewed from the outer surface of the packaging body 1X, the interval between the surface recesses 13 is shorter than the interval between the sheet recesses 24. In the packaging sheet 10X made of a film, the more the surface recess 13 is, the more the deformation starting point becomes, and it is easy to be deformed. Since the interval between the surface recesses 13 is relatively short, it is easy to secure flexibility of the packaging sheet 10X. Meanwhile, since the fibers of the nonwoven fabric are dense at a portion in which the sheet recess 24 is formed, it is easy for the nonwoven fabric to become hard. For this reason, the exterior sheet 21 made of the nonwoven fabric is less likely to be deformed as the number of sheet recesses 24 increases. Since the interval between the sheet recesses 24 is relatively long, it is easy to secure flexibility of the absorbent article 20. Therefore, the packaging sheet 10X and the absorbent article 20 are easily deformed more flexibly, and it is easy for the user to recognize that the absorbent articles are the absorbent articles which are soft and mild to a skin. In addition, since the interval between the surface recesses 13 is relatively narrow, the force is likely to be transferred to a large number of surface recesses 13 when the user presses the outer surface of the packaging body 1X, such that it is easier to deform the packaging sheet 10X. Therefore, the user can feel softness of the absorbent articles 20 or recall a soft image thereof.

The surface recesses 13 are irregularly disposed on a region in which the wearer image 15 is provided. If regular surface recesses 13 are formed in the wearer image 15, a regular pattern is formed in the wearer image, and it is difficult to form the texture such as the skin. In general, the convexoconcaves on the surface of the skin of the person are not regular dot or line shapes but are irregularly formed. As the surface recesses 13 are irregularly formed, the texture of the skin of the wearer image can be further increased to increase aesthetics.

A depth D1 of the surface recess 13 is shallower than a depth D2 of the back surface recess 14. Since the surface recess 13 is formed on the printing layer 12 and the film layer 11, the depth D1 of the surface recess 13 is a depth in a state in which the printing layer 12 is provided on the film layer 11 and is a distance in the thickness direction between the top face of the surface side of the printing layer 12 and the bottom face of the printing layer 12. The depth D2 of the back surface recess 14 is a distance in the thickness direction between the top face of the back surface side of the film layer 11 and the bottom face of the film layer 11.

Since the depth of the surface recess 13 is relatively shallow, a contact area between a finger and a surface 10T of the packaging sheet 10X can be secured to be widened when the finger of the user is in contact with the surface of the packaging sheet 10X. For this reason, a force pressed by the user is more easily transferred to the packaging sheet 10X and the absorbent articles 20, so that flexible deformation of the packaging sheet 10X and the absorbent articles 20 can be realized. In addition, since the depth of the back surface recess 14 is relatively deep, an area of the back surface recess 14 is increased such that a contact area between the back surface 10B of the packaging sheet 10X and the absorbent article 20 is easily reduced. In addition, due to a relatively deep depth of the back surface recess 14, even if a region between the back surface recesses 14 is collapsed, it is difficult for the region to be collapsed up to the bottom face of the back surface recess 14, and the contact area between the back surface 10B of the packaging sheet 10X and the absorbent article 20 is easily reduced. The contact area between the absorbent article 20 and the back surface 10B of the packaging sheet 10X is small so that when the force is transferred to the absorbent article 20 through the packaging sheet 10, an action point of the force is reduced and the force is concentrated on the action point. Therefore, the packaging sheet 10X and the absorbent article 20 are easily deformed more flexibly, and it is easy for the user to recognize that the absorbent articles 20 are the absorbent articles which are soft and mild to a skin.

In addition, a depth D3 of the surface recess 13 of the film layer 11 is shallower than the depth D2 of the back surface recess 14 of the film layer 11. The depth D3 of the surface recess 13 of the film layer 11 is a depth that does not include the printing layer 12, and is a distance in the thickness direction between the top face of the surface side of the film layer 11 and the bottom face of the film layer 11. When a printing is performed on the packaging sheet 10X, the printing layer 12 can be provided on the film layer 11 after forming the surface recesses 13 and the back surface recesses 14 on the film layer 11. In this case, since the depth of the surface recess 13 is relatively shallow, it is easy to form the printing layer 12 on the entire film layer 11 without stains. By forming the printing layer 12 without stains, the aesthetics of the packaging sheet 10X can be further increased.

The packaging sheet 10X according to the present embodiment can be acquired by performing the printing after embossing the film layer having a thickness of 0.04 mm to 0.20 mm. More preferably, the thickness of the film layer is 0.05 mm or more and 0.08 mm or less. The embossing is performed by passing the film layer 11 between a pair of rolls. The pair of rolls has a first roll having the projection corresponding to the back surface recess 14 provided on the outer peripheral surface thereof and a second roll having a flat outer peripheral surface. By passing the film layer 11 between the pair of rolls, the back surface recess 14 is formed by the projection of the first roll, and the film layer 11 is pulled along with the formation of the back surface recess 14, such that the projection is formed on the surface corresponding to the thickness direction of the back surface recess 14 and the surface recess 13 is formed in a region other than the back surface recess 14. The depth D2 of the back surface recess formed as described above is deeper than the depth D3 of the surface recess 13 of the film layer 11. Next, the printing is performed on the surface side of the film layer 11. A printing method is not particularly limited, and a flexo printing can be exemplified. The depth D2 of the back surface recess 14 is 50% or more of the thickness of the packaging sheet 10X and the depth D1 of the surface recess 13 is less than 50% of the thickness of the packaging sheet 10X. It is preferable that the depth D1 of the surface recess 13 is 10 μm to 50 μm, and it is preferable that the depth D2 of the back surface recess 14 is 40 μm to 70 μm. In order to form the printing layer 12 without stains, it is preferable that the depth of the surface recess 13 of the film layer 11 is less than 30 μm.

An embossing rate of the surface recess 13 is 10% or more and 80% or less, and an embossing rate of the back surface recess 14 is 20% or more and 90% or less. The embossing rate is a ratio of an area of the surface recess 13 or the back surface recess 14 per unit area. By such an embossing rate of the surface recesses 13 and the embossing rate of the sheet recesses described above, it is easy for the packaging sheet and the absorbent articles to be flexibly further deformed together. It is easy for the user to recognize that the absorbent articles are the absorbent articles which are soft and mild to a skin, so that the desire of purchase of the user can be further increased. The packaging sheet 10X has the embossing, whereby the number of deformation starting points is increased and it is easy for the packaging sheet 10X to be flexibly deformed. Therefore, when the user presses the packaging sheet with the finger, the packaging sheet is attached around the finger such that a contact area between the finger and the packaging sheet is increased. Due to the increased contact area between the finger and the packaging sheet 10X, the user is easy to feel the packaging sheet smooth.

A firmness of the packaging sheet 10X may be 46.3 mm or more and 52.4 mm or less. According to such a packaging sheet, a drape property is improved and it is easy for the packaging sheet to be flexibly deformed. A bending stiffness of the packaging sheet 10X is $0.064 \times 10^{-4}$ Nm/m or more and $0.077 \times 10^{-4}$ Nm/m or less. According to such a packaging sheet, when the user presses the packaging sheet with the finger, it becomes easy for the packaging sheet to be easily deformed. The bending hysteresis (bending resiliency) of the packaging sheet 10X is $0.030 \times 10^{-4}$ Nm/m or more and $0.007 \times 10^{-4}$ Nm/m or less. According to such a packaging sheet, when the user presses the packaging sheet with the finger, it is easy for the deformation to be recovered.

The bending stiffness of the packaging sheet is lower than the bending stiffness of the absorbent article. Since the bending stiffness of the packaging sheet is relatively low, the packaging sheet is easily deformed when the user presses the packaging sheet, and the absorbent article is more easily deformed through the packaging sheet.

As illustrated in FIGS. 1 and 2, the constricted portion 18 which is recessed toward the back surface 10B side of the packaging sheet 10X (the inner surface side of the packaging body 1X) is formed on the packaging sheet 10X. When the user presses the vicinity of the constricted portion 18 with the finger, a region having a small thickness of the absorbent article is laminated in the vicinity of the constricted portion, so that the finger tends to squeeze deeply into the constricted portion even with a small force. In addition, when the user presses the constricted portion 18 with the finger, the finger squeezes into the constricted portion and a contact area between the finger and the packaging sheet 10X is increased. Therefore, it is easier to recognize the absorbent articles which are soft and mild to the skin and the desire of purchase of the user can be further increased.

As illustrate in FIG. 9, the surface recesses 13 and the back surface recesses 14 cross the perforation 17 of the packaging sheet 10X. At least portion of the surface recesses 13 and the back surface recesses 14 may cross the perforation 17, and a portion thereof is disposed along the perforation 17. Specifically, the surface recess 13 has a first portion 13A extending in a direction along the perforation 17, and a second portion 13B extending in a direction crossing the perforation 17. The first portion 13A is a portion that is less than 45 degrees with respect to the direction in which the perforation 17 extends, and the second portion 13B is a portion that is 45 degrees or less with respect to a direction orthogonal to the direction in which the perforation 17 extends. In a region in which the perforation 17 is provided, the number of the second portions 13B is larger than the number of the first portions 13A. Since a thickness is different between the portion in which the surface recesses 13 are formed and the portion in which the surface recesses 13 are not formed, a sound produced at the time of fracture of the perforation 17 differs. For this reason, if the surface recesses 13 are parallel to the perforation 17, a frequency of the sound generated at the time of breaking of the perforation 17 is constant, and it is easy to feel the sound greatly. Meanwhile, if the surface recesses 13 cross the perforation 17, a frequency of the sound generated at the time of breaking of the perforation 17 is dispersed, and it is easy to feel the sound small.

In addition, the tear strength of the perforation 17 differs in the region in which the surface recesses 13 are provided and the region in which the surface recesses 13 are not provided. Since the number of the second portions 13B is relatively great in the region in which the perforation 17 is provided, a point at which the tear strength of the perforation 17 changes is increased and it is difficult for the perforation to be tore at one time. For this reason, it is possible to suppress an inadvertent increase of the extraction opening.

Figure 10:
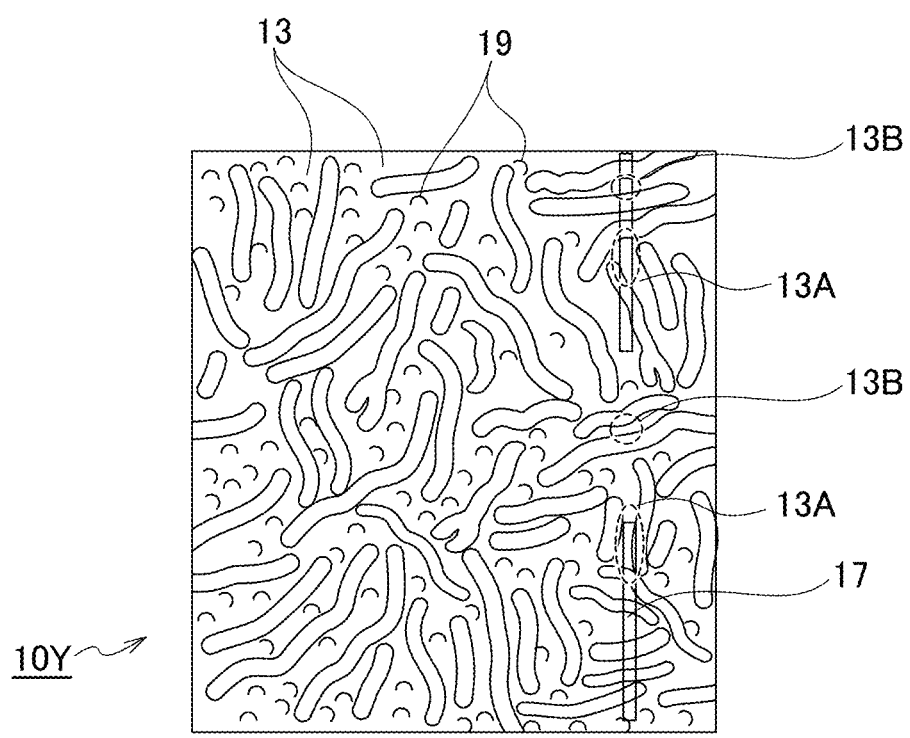
FIG. 10 is a plan view schematically illustrating a surface of a packaging sheet according to a modified example.

Next, a packaging sheet 10Y according to a modified example in the second embodiment will be described with reference to FIG. 10. Further, a cross section of the packaging sheet 10Y according to the modified example of the second embodiment is the same as that of the packaging sheet according to the modified example of the first embodiment illustrated in FIG. 7. FIG. 10 is a plan view of the packaging sheet 10Y according to a modified example of the second embodiment. By providing the fine projections 19, the fine projections 19 also constitute deformation starting points of the packaging sheet 10Y such that it becomes easier to deform the fine projections 19. In addition, in general, regions between the recesses constituting the skin texture of the person is not a smooth plane and have fine convexoconcaves formed therein. By providing the fine projections 19, the texture of the skin of the wearer image can be further increased to increase aesthetics.

Third Embodiment

Figure 11:
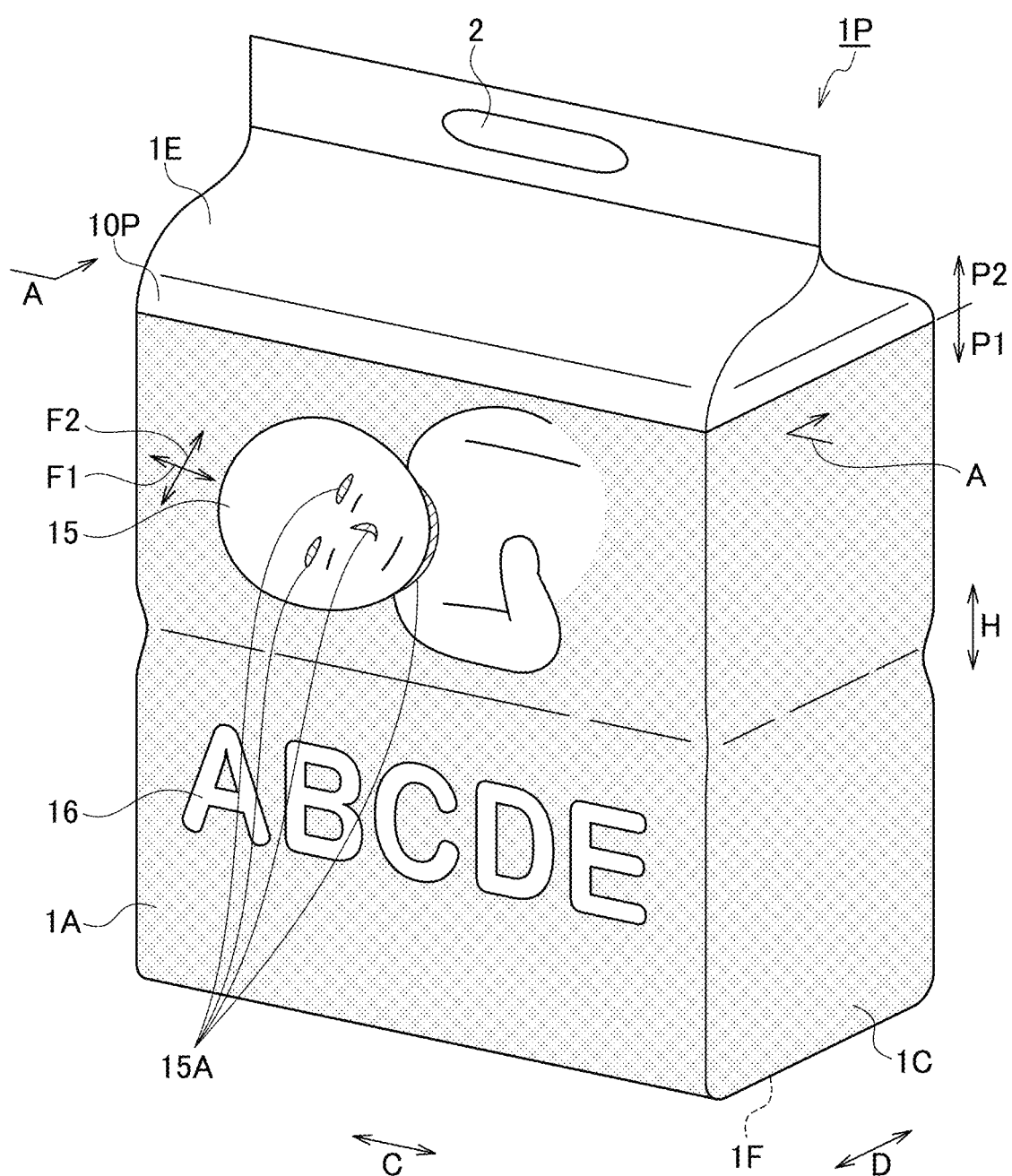
FIG. 11 is a perspective view of a front side of a packaging body for an absorbent article according to a third embodiment.
Figure 12:
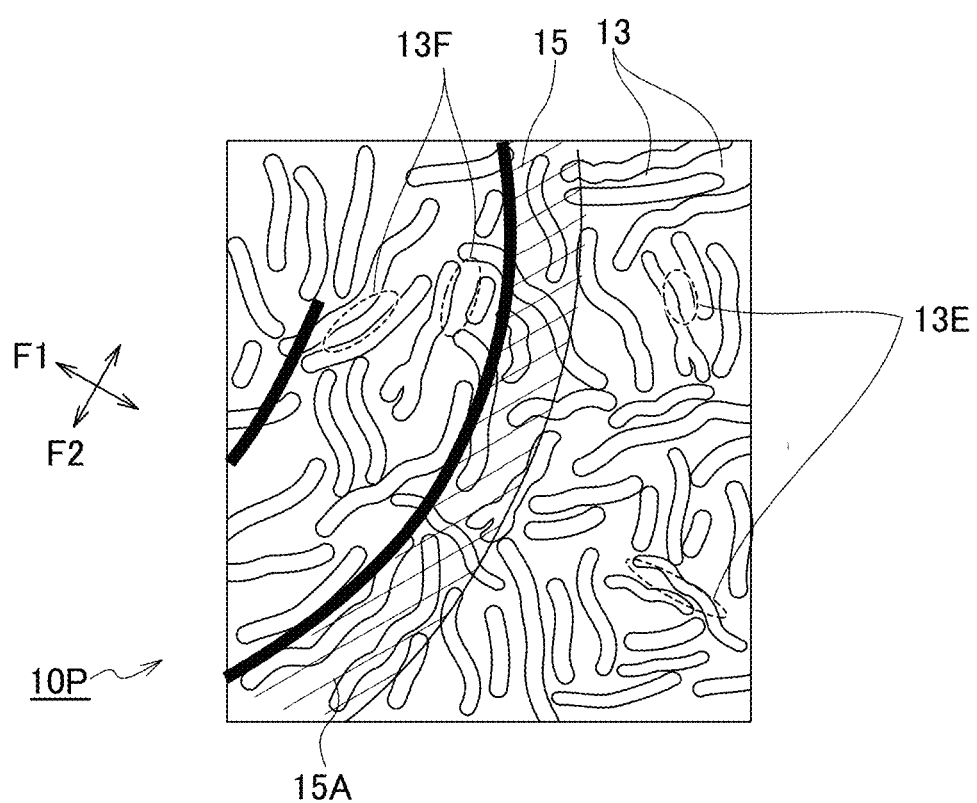
FIG. 12 is a plan view schematically illustrating a surface of a packaging sheet according to the third embodiment.

Next, a packaging body 1P for absorbent articles according to a third embodiment will be described. The overall structure of the packaging body according to the third embodiment is the same as that of the packaging body according to the first embodiment. FIGS. 2 to 5 and FIG. 7 illustrate the packaging body according to the third embodiment. Reference symbol 1 in FIGS. 2 to 5 and FIG. 7 denotes the packaging body 1P according to the third embodiment and reference symbol 10 in the drawings also denotes the packaging sheet 10P according to the third embodiment. FIG. 11 is a perspective view of a front side of a packaging body 1P for an absorbent article according to a third embodiment and FIG. 12 is a plan view schematically illustrating a surface of a packaging sheet 10P according to the third embodiment.

The sheet recesses and the sheet projections are formed on the exterior sheet 21 of the absorbent article 20. As illustrated in FIG. 4, by disposing the packaging sheet 10P along the sheet recesses 24 and the sheet projections 23, the convexoconcaves along the shape of the sheet recesses 24 or the like are formed on the packaging sheet 10P, so that a more stereoscopic visual effect can be exhibited.

The packaging sheet 10P includes a film layer 11 and a printing layer 12 provided on a surface side of the film layer 11. A thickness T2 of the printing layer on the bottom face of the surface recess 13 can be thicker than a thickness T1 of the printing layer 12 on the top face of the surface recess. Since the thickness T2 of the printing layer on the bottom face of the surface recess 13 is relatively thick, an image of the bottom face of the surface recess 13 can be made dark and a stereoscopic visual effect can be exhibited.

A wearer image 15 representing an image of a wearer and an identification image 16 displaying identification information such as a product name, or the like are provided in the printing region P1 of the packaging sheet. The wearer image 15 is an image for indicating a target wearer, and includes a face of the target wearer and a part of a body thereof. The wearer image 15 has shadow portions 15A indicating shadows due to the convexoconcaves of the face. The shadow portions 15A are portions indicating the shadows that appear around, for example, a nasolabial fold, inner corners of eyes, eyebrows, and nose.

A plurality of surface recesses 13 which are recessed toward the back surface 10B side of the packaging sheet 10P are formed on the surface 10T of the packaging sheet 10P. A plurality of back surface recesses 14 which are recessed toward the surface 10T side of the packaging sheet 10P are formed on the back surface 10B of the packaging sheet 10P. The surface recesses are irregularly disposed on a region which at least overlaps with the wearer image 15. Further, the shape and arrangement of the surface recesses 13 in a region which does not overlap with the wearer image is not limited, may be, for example, a dot or a polygonal shape, may be a regular arrangement such as a zigzag shape or a grid-like dotted line shape, may be an irregular curved shape, may be an irregular straight line shape, or may be a combination thereof. Similarly, the shape and arrangement of the back surface recesses 14 are not limited.

The surface recesses 13 and the back surface recesses 14 are alternately disposed when viewed in plan. Specifically, the surface recesses 13 overlap with regions in which the back surface recesses 14 are not formed, and the back surface recesses 14 overlap with regions in which the surface recesses 13 are not formed. Further, the surface recesses 13 and the back surface recesses 14 may partially overlap. The regions of the surface recesses 13 and the regions of the back surface recesses 14 are recessed regions than a midpoint between the surface and the back surface of the packaging sheet 10P.

The surface recesses 13 are recessed toward the back surface 10B side on the surface 10T of the packaging sheet 10P to thereby constitute the packaging recesses according to the present invention. The surface recesses 13 are irregularly disposed on a region which overlaps with the wearer image 15. Since the surface recesses 13 are provided to be overlapped with the wearer image 15, light incident on the surface 10T of the packaging sheet 10P is diffusely reflected compared with a smooth packaging sheet, and the wearer image 15 can be stereoscopically displayed. Further, the convexoconcaves are formed on the wearer image 15 by the surface recesses 13 to form depth feeling, such that the wearer image 15 can be stereoscopically displayed.

In general, since the skin texture is irregularly constituted, it is difficult to generate the texture such as the skin when a regular pattern is formed on the wearer image 15. In addition, when a regular dot pattern is formed on the wearer image 15, the dot reminds an eruption, so that it is difficult to generate good skin texture. In general, a skin texture (skin) of a person is not a regular dot or line shape but an irregular shape. Since the surface recesses 13 are irregularly disposed, the texture such as the skin can be given to the wearer image 15.

As illustrated in FIG. 12, the surface recess 13 includes a vertical portion 13E along a vertical direction F1 of the face of the wearer image 15, and a second portion 13B along a direction F2 orthogonal to the vertical direction F1. The vertical portion 13E is a portion that is less than 45 degrees with respect to the vertical direction F1. An orthogonal portion 13F is a portion that is 45 degrees or less with respect to a direction F2 orthogonal to the vertical direction. The surface recess 13 has a curved shape having the vertical portion 13E and the orthogonal portion 13F. At least one surface recess 13 among the plurality of surface recesses 13 may be constituted while having both the vertical portion 13E and the orthogonal portion 13F, and the surface recess 13 having only the vertical portion or the surface recess having only the orthogonal portion may be provided. The surface recess 13 of the curved shape having the vertical portion 13E and the orthogonal portion 13F may be overlapped with at least a portion of the wearer image 15. The surface recess 13 of a straight line shape, the surface recess 13 having only the vertical portion 13E, or the surface recess 13 having only the orthogonal portion 13F may be overlapped with the wearer image 15. In general, the skin texture does not extend in a certain direction but extends in various directions. In addition, the skin texture is not a straight line shape but a curved line shape. Since the surface recesses 13 are the curved shapes having the vertical portions and the orthogonal portions, the surface recesses 13 can more exhibit visual effects such as the skin texture, and the texture of the wearer image can be further improved. More preferably, a leather pattern or a satin pattern having a curved shape is preferable. In addition, by combining the surface recesses 13 of a plurality of patterns having different depths, it is possible to bring the surface recesses 13 closer to the texture of actual skin. Such a leather pattern or a satin pattern can be formed by molding a shape of an arbitrary pattern such as a leather pattern or a satin pattern on the surface of a mold and surface-texturing it with the mold.

The surface recesses 13 are provided in a region overlapping the shadow portions 15A of the wearer image 15. The face of the person is three-dimensional, and the shadows appear around, for example, a nasolabial fold, inner corners of eyes, eyebrows, and nose. Since the surface recesses 13 are formed in the shadow portions 15A indicating the shadows of the wearer image 15, the shadows due to the convexoconcave shapes of the surface recesses 13 occur and a stereoscopic effect of the wearer image can be further increased. In addition, by providing shadows by printing in conjunction with shadows due to the convexoconcave shape of the surface recesses 13, visual effects such as shadows can be exhibited and the stereoscopic effect of the wearer image 15 is improved.

An area of the orthogonal portion 13F in a region overlapping with the wearer image 15 may be larger than an area of the vertical portion 13E. The skin texture of the person may have a high ratio in the portion extending in the orthogonal direction F2 than portion extending in the vertical direction F1 of the face. Since an area ratio of the orthogonal portion 13F is high in the region overlapping with the wearer image 15, the texture such as the skin can be represented and the skin texture of the wearer image 15 can be further increased.

A width of the surface recess 13 and a width of the back surface recess 14 are 0.15 mm or more and 2.0 mm or less, respectively. In a state in which the width of the surface recess 13 and the width of the back surface recess 14 are not constant, a maximum width may be 2.0 mm or less and a minimum width may be 0.15 mm or more. Preferably, the width of the surface recess may be 0.15 mm or more and 2.0 mm or less, and the width of the back surface recess may be 0.30 mm or more and 2.0 mm or less. A length of the surface recess 13 is longer than the width of the surface recess 13, and a length of the back surface recess 14 is longer than the width of the back surface recess 14. Further, the length of the surface recess 13 may be the same as the width of the surface recess 13, and may be shorter than the width of the surface recess 13. The length of the back surface recess 14 may be the same as the width of the back surface recess 14, and may be shorter than the width of the back surface recess 14. By the surface recesses 13 having such dimensions, since it is easier for the surface recesses to exhibit the visible effect such as the skin texture, the texture such as the skin can be given to the wearer image.

An interval between the surface recesses 13 and an interval between the back surface recesses 14 are 0.15 mm or more and 2.0 mm or less, respectively. Preferably, the interval between the surface recesses may be 0.1 mm or more and 1.0 mm or less, and the interval between the back surface recesses may be 0.15 mm or more and 2.0 mm or less. More preferably, the interval may be 0.8 mm or less. More preferably, the interval between the surface recesses 13 may be 0.1 mm or more and 1.0 mm or less. In general, an interval between the skin textures is often 0.1 mm or more and 1.0 mm or less. By setting the interval between the surface recesses 13 to 0.1 mm or more and 1.0 mm or less, the texture such as the skin can be represented and the skin texture of the wearer image 15 can be increased.

A depth D1 of the surface recess 13 is shallower than a depth D2 of the back surface recess 14. A depth D3 of the surface recess 13 of the film layer 11 is shallower than the depth D2 of the back surface recess 14 of the film layer 11. When a printing is performed on the packaging sheet 10P, the printing layer 12 can be provided on the film layer 11 after forming the surface recesses 13 and the back surface recesses 14 on the film layer 11. In this case, since the depth of the surface recess 13 is relatively shallow, it is easy to form the printing layer 12 on the entire film layer 11 without stains. By forming the printing layer 12 without stains, an image quality of the wearer image 15 can be improved and the texture of the wearer image 15 can be increased.

The packaging sheet 10P is not entirely printed, but has a printing region P1 and a non-printing region P2. A depth D1 of the surface recess 13 of the printing region P1 and a depth of the surface recess 13 of the non-printing region P2 are different from each other. The depth of the surface recess 13 of the non-printing region P2 is the depth D3 of the surface recess 13 of the film layer 11. Light incident on the printing region P1 of the packaging sheet 10P and light incident on the non-printing region P2 are reflected in different modes. Since the packaging sheet 10P is more visible than the packaging sheet of the flat surface and attracts the attention of the user, the desire of purchase of the user can be increased. In addition, since the wearer image 15 of the printing region P1 differs not only in the presence or absence of printing, but also in the reflection mode of light with respect to the non-printing region P2, the wearer image 15 is more visible and can attract the attention of the user. Further, since the depth D1 of the surface recess 13 provided on the wearer image 15 is relatively shallow, the texture of the wearer image 15 can be smoothened. The texture such as the skin due to the diffused reflection of light can be obtained while exhibiting a smooth visual effect of the wearer image 15.

In addition, after the printing layer 12 is provided on the film layer 11, the surface recesses 13 may be formed. By forming the surface recesses 13, the printing layer 12 may be partially scratched. The printing layer 12 is provided in a partially different manner, so that it becomes visible in comparison with the packaging sheet 10P of a uniform printing layer over an entire surface.

In addition, the packaging sheet according to the present embodiment has the back surface recesses 14 formed on the back surface 10B, and the surface recesses 13 and the back surface recesses 14 are alternately formed when viewed in plane. For example, in the packaging sheet 10P in which only the surface recesses 13 are provided and the back surface 10B side is a smooth surface, a thickness of a portion in which the surface recesses 13 are formed becomes thin. Meanwhile, by the packaging sheet 10P in which the back surface recesses 14 are provided on the back surface 10B side, and the surface recesses 13 and the back surface recesses 14 are alternately formed, the surface recesses 13 can be formed deep while securing the thickness of the sheet itself. Therefore, a more stereoscopic visual effect can be exhibited.

The packaging sheet 10P according to the present embodiment can be acquired by performing the printing after embossing the film layer having a thickness of 0.04 mm to 0.20 mm. More preferably, the thickness of the film layer is 0.05 mm or more and 0.08 mm or less. The embossing is performed by passing the film layer 11 between a pair of rolls. The pair of rolls has a first roll having the projection corresponding to the back surface recess 14 provided on the outer peripheral surface thereof and a second roll having a flat outer peripheral surface. By passing the film layer 11 between the pair of rolls, the back surface recess 14 is formed by the projection of the first roll, and the film layer 11 is pulled along with the formation of the back surface recess 14, such that the projection is formed on the surface corresponding to the thickness direction and the surface recess 13 is formed in a region other than the back surface recess 14. The depth D2 of the back surface recess formed as described above is deeper than the depth D3 of the surface recess 13 of the film layer 11. Next, the printing is performed on the surface side of the film layer 11. A printing method is not particularly limited, and a flexo printing can be exemplified. The depth D2 of the back surface recess 14 is 50% or more of the thickness of the packaging sheet 10P and the depth D1 of the surface recess 13 is less than 50% of the thickness of the packaging sheet 10P.

It is preferable that the depth D1 of the surface recess 13 is 10 μm to 50 μm, and it is preferable that the depth D2 of the back surface recess 14 is 40 μm to 70 μm. In order to form the printing layer 12 without stains, it is preferable that the depth of the surface recess 13 of the film layer 11 is less than 30 μm.

An embossing rate of the surface recess 13 is 10% or more and 80% or less, and an embossing rate of the back surface recess 14 is 20% or more and 90% or less. The embossing rate is a ratio of an area of the surface recess 13 or the back surface recess 14 per unit area. By such an embossing rate, an effect of increasing the skin texture and stereoscopic effect of the wearer image is more easily obtained.

A firmness of the packaging sheet 10P may be 46.3 mm or more and 52.4 mm or less. According to such a packaging sheet, a drape property is improved and it is easy for the packaging sheet to be flexibly deformed. A bending strength of the packaging sheet 10P is $0.064 \times 10^{-4}$ Nm/m or more and $0.077 \times 10^{-4}$ Nm/m or less. According to such a packaging sheet, it is easy for the packaging sheet to be flexibly deformed. The bending hysteresis (bending resiliency) of the packaging sheet 10P is $0.030 \times 10^{-4}$ Nm/m or more and $0.007 \times 10^{-4}$ Nm/m or less. By such a packaging sheet, it is easy to recover the deformation such that more soft texture can be exhibited.

The bending stiffness of the packaging sheet is lower than the bending stiffness of the absorbent article. Since the bending stiffness of the packaging sheet is relatively low, it is easy to deform the packaging sheet.

Figure 13:
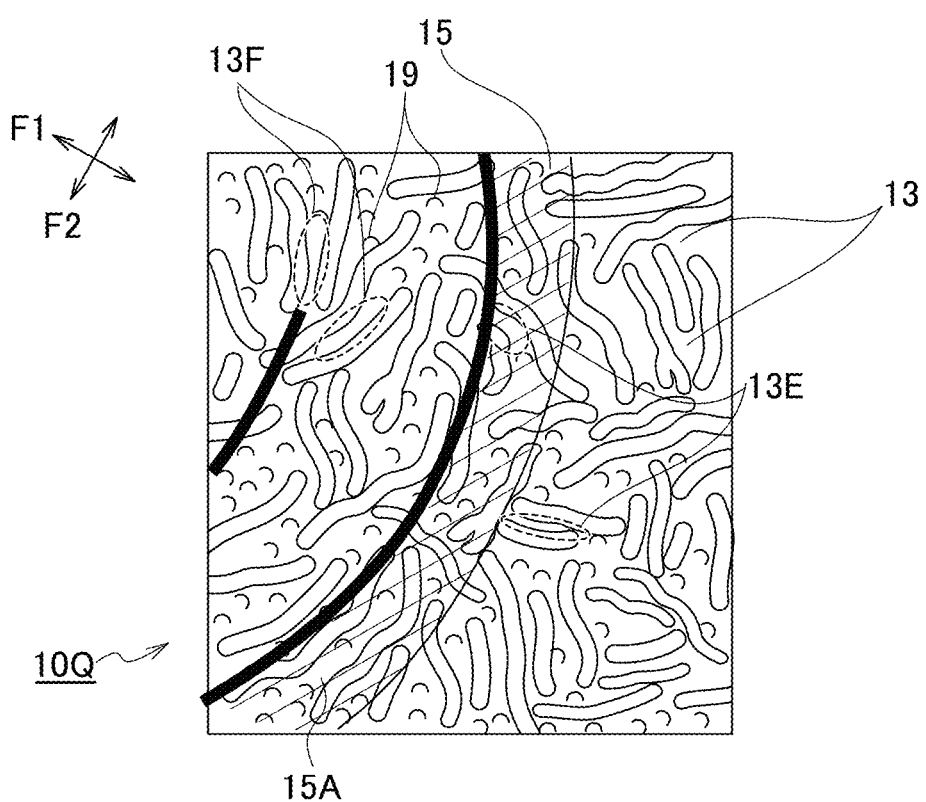
FIG. 13 is a plan view schematically illustrating a surface of a packaging sheet according to a modified example.

Next, a packaging sheet 10Q according to a modified example in the second embodiment will be described with reference to FIG. 13. Further, a cross section of the packaging sheet 10Q according to the modified example in the third embodiment is the same as that of the packaging sheet according to the modified example in the first embodiment illustrated in FIG. 7. FIG. 13 is a plan view of the packaging sheet 10Q according to a modified example of the third embodiment.

The surface recesses 13 and the fine projections 19 are formed on the surface of the packaging sheet 10Q according to the modified example, and the stereoscopic effect can be further increased by the recesses having different depths. In addition, in general, regions between the recesses constituting the skin texture of the person is not a smooth plane and have fine convexoconcaves formed therein. By providing the fine projections 19, the texture of the skin of the wearer image can be further increased to increase aesthetics.

Although the present invention has been described in detail with reference to the above embodiments, it is obvious to those skilled in the art that the present invention is not limited to the embodiments described herein. The present invention may be embodied as modifications and variations without departing from the spirit and scope of the invention as defined by the appended claims. Therefore, the description herein is for illustrative purposes only and is not meant to limit the present invention.

In addition, the entire contents of Japanese Patent Application No. 2016-208158, Japanese Patent Application No. 2016-208161 and Japanese Patent Application No. 2016-208162 filed on Oct. 24, 2016 are incorporated herein by reference.

INDUSTRIAL APPLICABILITY

The packaging body for absorbent articles which can further attract the attention of the user and can increase the desire of purchase of the user can be provided.

REFERENCE SIGNS LIST

1: packaging body for absorbent articles
10: packaging sheet
11: film layer
12: printing layer
13: surface recess
13A: first portion
13B: second portion
13E: vertical portion
13F: orthogonal portion
14: back surface recess
17: perforation
18: constricted portion
20: absorbent article
21: exterior sheet
23: sheet projection
24: sheet recess (article recess)
25: laminate member
P1: printing region
P2: non-printing region

The invention claimed is:

1. A packaging body for absorbent articles, the packaging body comprising:
a plurality of absorbent articles; and
a bag-shaped packaging sheet that packages the plurality of absorbent articles, wherein
the packaging sheet includes
a surface that constitutes an outer surface of the packaging body, and
a back surface that constitutes an inner surface of the packaging body and comes into contact with the absorbent articles,
the surface of the packaging sheet has a plurality of surface recesses formed so as to be recessed toward the back surface,
the back surface of the packaging sheet has a plurality of back surface recesses formed so as to be recessed toward the surface,
the packaging body includes laminate members in which the absorbent articles are laminated in a thickness direction of the absorbent articles,
the laminate members are laminated in an orthogonal direction orthogonal to the thickness direction,
the packaging sheet has constricted portions formed so as to be recessed toward the back surface, and
the constricted portions are formed along a boundary between the laminate members.

2. The packaging body according to claim 1, wherein
the absorbent articles include an exterior sheet disposed on outer surfaces of the absorbent articles, and
the exterior sheet is made of non-woven fabric and comes into contact with the back surface recesses of the packaging sheet.

3. The packaging body according to claim 2, wherein
the exterior sheet has a plurality of sheet projections protruding in the thickness direction of the absorbent articles and sheet recesses disposed between the sheet projections, and
the sheet projections and the sheet recesses come into contact with the back surface recesses, respectively.

4. The packaging body according to claim 1, wherein
a width of the surface recess and a width of the back surface recess are 0.15 mm or more and 2.0 mm or less, respectively, and
an interval between the surface recesses and an interval between the back surface recesses are 0.15 mm or more and 2.0 mm or less, respectively.

5. The packaging body according to claim 1, wherein
the surface recesses and the back surface recesses are embossed,
an embossing rate of the surface recesses is 10% or more and 80% or less, and
an embossing rate of the back surface recesses is 20% or more and 90% or less.

6. The packaging body for absorbent articles according to claim 1, wherein
the packaging sheet has a perforation to form an extraction opening of the absorbent articles, and
the surface recesses and the back surface recesses cross the perforation.

7. The packaging body according to claim 1, wherein
a mean deviation (MMD) of a surface friction coefficient of the surface of the packaging sheet is 0.0056 or more and 0.0257 or less,
a mean deviation (MMD) of a surface friction coefficient of the back surface of the packaging sheet is 0.0061 or more and 0.0258 or less,
a mean deviation (SMD) of surface roughness of the surface of the packaging sheet is 0.8504 or more and 4.4314 or less, and a mean deviation (SMD) of surface roughness of the back surface of the packaging sheet is 1.0942 or more and 3.4088 or less.

8. A packaging body for absorbent articles, the packaging body comprising:
a plurality of absorbent articles; and
a bag-shaped packaging sheet that packages the plurality of absorbent articles, wherein
the packaging sheet includes
a surface that constitutes an outer surface of the packaging body, and
a back surface that constitutes an inner surface of the packaging body and comes into contact with the absorbent articles,
the surface of the packaging sheet has a plurality of surface recesses formed so as to be recessed toward the back surface,
the back surface of the packaging sheet has a plurality of back surface recesses formed so as to be recessed toward the surface,
the packaging sheet includes
a film layer, and
a printing layer provided on a side of the film layer facing the surface,
the surface recesses are formed on the film layer and the printing layer, and
a depth of the surface recess of the film layer is shallower than a depth of the back surface recess of the film layer.

9. A packaging body for absorbent articles, the packaging body comprising:
a plurality of absorbent articles; and
a bag-shaped packaging sheet that packages the plurality of absorbent articles, wherein
the packaging sheet includes
a surface that constitutes an outer surface of the packaging body, and
a back surface that constitutes an inner surface of the packaging body and comes into contact with outer surfaces of the absorbent articles,
a plurality of surface recesses which are recessed in a thickness direction of the packaging sheet are formed on the surface of the packaging sheet,
a plurality of article recesses which are recessed in a thickness direction of the absorbent articles are formed on the outer surfaces of the absorbent articles,
the surface recesses are provided on regions overlapping the article recesses,
the packaging sheet has a perforation to form an extraction opening of the absorbent articles,
the surface recess includes a first portion extending in a direction along the perforation and a second portion extending in a direction crossing the perforation, and
the number of the second portions in a region in which the perforation is provided is greater than the number of the first portions.

10. The packaging body according to claim 9, wherein a plurality of back surface recesses which are recessed in the thickness direction of the packaging sheet are formed on the back surface of the packaging sheet, and
a depth of the surface recess is shallower than a depth of the back surface recess.

11. The packaging body according to claim 9, wherein a bending stiffness of the packaging sheet is lower than a bending stiffness of the absorbent article.

12. The packaging body according to claim 9, wherein a width of the surface recess is 0.15 mm or more and 2.0 mm or less,
an interval between the surface recesses is 0.15 mm or more and 2.0 mm or less,
a width of the article recess is 0.25 mm or more and 5.0 mm or less, and
an interval between the article recesses is 0.5 mm or more and 20.0 mm or less.

13. The packaging body according to claim 9, wherein the surface recesses and the article recesses are embossed,
an embossing rate of the surface recesses is 10% or more and 80% or less, and
an embossing rate of the article recesses is 1% or more and 90% or less.

14. The packaging body according to claim 9, wherein a firmness of the packaging sheet is 46.3 mm or more and 52.4 mm or less,
a bending stiffness of the packaging sheet is $0.064 \times 10^{-4}$ Nm/m or more and $0.077 \times 10^{-4}$ Nm/m or less, and
a bending hysteresis of the packaging sheet is $0.030 \times 10^{-4}$ Nm/m or more and $0.007 \times 10^{-4}$ Nm/m or less.

15. A packaging body for absorbent articles, the packaging body comprising:
a plurality of absorbent articles; and
a bag-shaped packaging sheet that packages the plurality of absorbent articles, wherein
the packaging sheet includes
a surface that constitutes an outer surface of the packaging body, and
a back surface that constitutes an inner surface of the packaging body and comes into contact with outer surfaces of the absorbent articles,
a plurality of surface recesses which are recessed in a thickness direction of the packaging sheet are formed on the surface of the packaging sheet,
a plurality of article recesses which are recessed in a thickness direction of the absorbent articles are formed on the outer surfaces of the absorbent articles,
the surface recesses are provided on regions overlapping the article recesses,
the packaging sheet is constituted by a film,
the outer surface of the absorbent article is constituted by a nonwoven fabric,
an interval between the surface recesses is shorter than an interval between the article recesses, and
the article recesses are embossed.

16. A packaging body for absorbent articles, the packaging body comprising:
a plurality of absorbent articles; and
a bag-shaped packaging sheet that packages the plurality of absorbent articles, wherein
the packaging sheet includes
a surface that constitutes an outer surface of the packaging body, and
a back surface that constitutes an inner surface of the packaging body and comes into contact with the absorbent articles,
a plurality of packaging recesses which are recessed toward the back surface and a wearer image representing a wearer of the absorbent articles are provided on the surface of the packaging sheet,
the packaging recesses are irregularly disposed in a region in which the wearer image is provided,
the packaging sheet includes
a film layer, and
a printing layer provided on a side of the film layer facing the surface,
the back surface of the packaging sheet has back surface recesses formed so as to be recessed toward the surface, the packaging recesses are formed on the film layer and the printing layer, and a depth of the packaging recess of the film layer is shallower than a depth of the back surface recess of the film layer.

17. The packaging body according to claim 16, wherein the packaging recesses include vertical portions along a vertical direction of a face of the wearer image and orthogonal portions along a direction orthogonal to the vertical direction, and the packaging recesses are curved shapes having the vertical portions and the orthogonal portions.

18. The packaging body according to claim 17, wherein the wearer image has shadow portions indicating shadows due to convexoconcaves of the face, and the packaging recesses are provided in regions overlapping the shadow portions.

19. The packaging body according to claim 16, wherein an interval between the packaging recesses is 0.1 mm or more and 1.0 mm or less.

20. The packaging body according to claim 16, wherein the packaging sheet includes a printing region having the film layer and the printing layer, and a non-printing region that has the film layer and does not have the printing layer, the wearer image is provided in the printing region, and a depth of the packaging recess in the printing region is shallower than the depth of the packaging recess in the non-printing region.

21. The packaging body according to claim 16, wherein a width between the packaging recesses is 0.15 mm or more and 2.0 mm or less.

22. The packaging body according to claim 16, wherein the packaging recesses are embossed, and an embossing rate of the packaging recesses is 10% or more and 80% or less.

23. The packaging body according to claim 16, wherein a firmness of the packaging sheet is 46.3 mm or more and 52.4 mm or less, a bending stiffness of the packaging sheet is $0.064 \times 10^{-4}$ Nm/m or more and $0.077 \times 10^{-4}$ Nm/m or less, and a bending hysteresis of the packaging sheet is $0.030 \times 10^{-4}$ Nm/m or more and $0.007 \times 10^{-4}$ Nm/m or less.

* * * * *